United States Patent
Lee et al.

(10) Patent No.: US 6,835,735 B2
(45) Date of Patent: Dec. 28, 2004

(54) 4-(PHENYLAMINO)-[1,4]DIOXANO[2,3-G] QUINAZOLINE DERIVATIVES AND PROCESS FOR PREPARING THE SAME

(75) Inventors: Yong-Sup Lee, Seoul (KR); Ho-Koon Park, Seoul (KR); Jae-Yeol Lee, Seoul (KR); Beom-Seok Yang, Seoul (KR); Seon-Hee Seo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 108 days.

(21) Appl. No.: 10/096,317

(22) Filed: Mar. 11, 2002

(65) Prior Publication Data

US 2003/0045537 A1 Mar. 6, 2003

(30) Foreign Application Priority Data

Jun. 28, 2001 (KR) .................................. 2001-0037867

(51) Int. Cl.$^7$ .................. A61K 31/519; C07D 491/056
(52) U.S. Cl. ........................................ 514/267; 544/250
(58) Field of Search ........................... 514/267; 544/250

(56) References Cited

U.S. PATENT DOCUMENTS 5,457,105 A * 10/1995 Barker .................... 514/234.5

FOREIGN PATENT DOCUMENTS

| EP | 0 520 722 A1 | 6/1992 |
| EP | 0 566 226 A1 | 1/1993 |
| EP | 0 602 851 A1 | 12/1993 |

OTHER PUBLICATIONS

Arteaga C.L. et. al., PubMed Abstract, PMID #15052538, Mar. 2004 (Seminars in Oncology, Supplement 3, vol. 31, No. 1 Feb. 2004, pp. 3–8).*

Fry, D.W. et al., A specific inhibitor of the Epidermal Growth Factor Receptor Tyrosine Kinase, Science, 265:1093–1095(1994).

Rewcastle, G.W. et al., Tyrosine Kinase Inhibitors. 5. Synthesis and Structure–Activeity Relationships for 4–[(Phenylmethyl) anubi]—and 4–(Phenylamino) quinazolines as Potent Adenosine 5'—Triphosphate Binding Site Inhibitors of the Tyrosine Kinase Domain of the Epidermal Growth Factor Receptor, J. Med. Chem., 38(18): 3482–3487 (1995).

Bridges, A.J. et al., Tyrosine Kinase Inhibitors. 8, An Unusually Steep Structure–Activity Relationship for Analoques of 4–(3–Bromoanilino)–6,7–dimethoxyquinazoline (PD 153035), a Potent Inhibitor of the Epidermal Growth Factor Receptor, J. Med Chem., 39(1):267–276 (1996).

Bianco, E. et al., Antitumor Activity of Combined. Treatment of Human Cancer Cells with Ionizing Radiation and Anti–Epidermal Growth Factor Receptor Monoclonal Antibody C225 plus Type I Protein Kinase A Antisense Oligonucleotice, Clin. Cancer Res., 6:4343–4350(2000).

Bolognesi, M. L. et al., WB 4101–Related Compounds. 2. Role of the Ethylene Chain Separating Amine and Phenoxy Units on the Affinity for α1–Adrenoreceptor Subtypes and 5–HT$_{1A}$ Receptors, J. Med. Chem., 42(20):4214–4224(1999).

Birch, A.M. et al., N–Substituted (2,3–Dihydro–1, 4–benzodioxin–2–yl) methylanine Derivatives as D$_2$ Antagonists/5–HT$_{1A}$ Partial Agonists with Potential as Atypical Antipsychotic Agents, J. Med. Chem., 42(17):3342–3355(1999).

Kitchin, J. et al., Synthesis of Benzodioxinopyrroles as Selective α$_2$–Andrenoceptor Antagonists, Bioorg. Med Chem., 3(12):1595–1603(1995).

* cited by examiner

*Primary Examiner*—Richard L. Raymond
(74) *Attorney, Agent, or Firm*—Knobbe, Martens, Olson & Bear, LLP

(57) ABSTRACT

The present invention relates to 4-(phenylamino)-[1,4] dioxano[2,3-g]quinazoline derivatives which inhibit tyrosine kinase of epidermal growth factor receptor(EGFR), and pharmaceutically acceptable salts, hydrates and solvates thereof, and a process for preparing the same. Since 4-(phenylamino)-[1,4]dioxano[2,3-g]quinazoline derivatives of the invention have a high solubility in water and inhibit the activity of EGFR tyrosine kinase and the growth of cancer cells, they can be practically applied in the treatment of overproliferation-associated diseases such as cancer.

19 Claims, No Drawings

4-(PHENYLAMINO)-[1,4]DIOXANO[2,3-G] QUINAZOLINE DERIVATIVES AND PROCESS FOR PREPARING THE SAME

BACKGROUND OF THE INVENTION

1. Field of the Invention

The present invention relates to 4-(phenylamino)-[1,4] dioxano[2,3-g]quinazoline derivatives and a process for preparing the same, more specifically, to 4-(phenylamino)-[1,4]dioxano[2,3-g]quinazoline derivatives which inhibit the activity of tyrosine kinase of epidermal growth factor receptor ("EGFR"), and pharmaceutically acceptable salts, hydrates and solvates thereof, and a process for preparing the same.

2. Discussion of Related Technology

Experimental approaches have been conventionally made in the art, to explore and develop anticancer agents. However, as cellular metabolism becomes clear in the level of protein by employing the biochemical techniques, nowadays, they are being replaced by the methods based on reaction mechanism. Such a reaction mechanism-based development of anticancer agents has been realized by targeting a variety of biological phenomena such as cytotoxicity, antibody, hormone antagonist, signal transduction inhibition, cell cycle control, cell death, angiogenesis inhibition, invasion inhibition, etc.

Up to date, low-priced anticancer agents have been developed by chemical synthesis, and most of anticancer agents used for clinical purposes exhibit their anticancer activities by inhibiting DNA synthesis or biological function. However, the said agents have several problems such as attacking DNA of normal cells as well as cancer cells to cause side effects and toxicity, and inducing resistance.

Meanwhile, under a consideration that the phosphorylation of tyrosine by regulating the activities tyrosine kinase and tyrosine phosphatase is necessary for controlling the growth and differentiation of normal cells, extensive studies have been lately made on the development of novel anticancer agents which possess a selectivity between normal and cancer cells, by way of targating on signal transduction. Among kinases taken part in the signal transduction during cell growth, tyrosine kinase is classified largely into non-transmembrane and transmembrane growth factor receptor tyrosine kinases, where the transmembrane growth factor binds to a cell surface receptor to form a dimer in the cytosolic domain of the receptor which is subsequently activated and phosphorylated. Activation of such receptors causes a signal transduction cascade which regulates diverse cellular responses. This transmembrane growth factor receptor tyrosine kinase is known to participate in a variety of biological phenomena in vivo such as angiogenesis, atherosclerosis and cancer, thus, it is expected to be a key element in the development of anticancer agents which effectively treat cancer without harmful side-effects. However, since a number of tyrosine and serine/threonine kinases whose ATP binding sites are structurally similar are retarding the development of inhibitors specific to tyrosine kinase of transmembrane growth factor receptor, extensive studies are in progress to overcome the problems.

Recently, various 4-(phenylamino)quinazoline compounds have been proposed in the art, which includes PD153035 possessing selective and powerful inhibitory effect ($IC_{50}$=29 pM) on tyrosine kinase of EGFR, known to be overexpressed in many human cancers, by way of competing with ATP (see: David W. Fry et al., Science, 265:1093–1095, 1994; Gordon W. Rewcastle et al., J. Med. Chem., 38:3482–3487, 1995; Alexander J. Bridges et al., J. Med. Chem., 39:267–276, 1996; WO 95/66226). However, it is difficult to evaluate in vivo pharmacological efficacy of the said compound using a tumor model because of its insolubility in water. Though ZD 1839(Iressa) to which a hydrophilic substituent is introduced was suggested in order to resolve the problem of insolubility, the said compound does not have a high solubility like the prior art compounds and shows a relatively low pharmacological efficacy.

Under the circumstances, there are strong reasons for exploring and developing 4-(phenylamino)quinazoline compounds which are highly soluble in water.

SUMMARY OF THE INVENTION

The present inventors have made an effort to develop novel 4-(phenylamino)quinazoline compounds possessing a high solubility in water, and finally found that 4-(phenylamino)-[1,4]dioxano[2,3-g]quinazoline derivatives effectively inhibit the activity of tyrosine kinase of EGFR and the growth of cancer cell, and exhibit a high solubility in water. A primary object of the present invention is, therefore, to provide 4-(phenylamino)-[1,4]dioxano[2,3-g]quinazoline derivatives which exhibit an inhibitory activity on tyrosine kinase, and pharmaceutically acceptable salts, hydrates and solvates thereof. The other object of the invention is to provide a process for preparing the same.

One aspect of the present invention provides a compound that has Formula I:

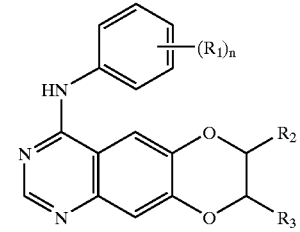

Formula (I)

or a pharmaceutically acceptable salt, hydrate or solvate thereof, wherein: n is 1, 2 or 3, $R_1$ is substituent group, may be identical or different when n is 2 or 3, and is selected from the group consisting of hydrogen, halogen, $C_{1-6}$-alkyl, $C_{3-6}$-cycloalkyl, hydroxy, $C_{1-6}$-alkoxy, $C_{3-6}$-cycloalkoxy, (aryl or heteroaryl)oxy, $C_{1-6}$-thioalkoxy, $C_{3-6}$-thiocycloalkoxy, thio (aryl or heteroaryl)oxy, nitro, amino, N-mono($C_{1-6}$)-alkylamino, N,N-di($C_{1-6}$)-alkylamino, formamido, amido, acetamido, hydroxyamino, $C_{1-6}$-alkoxyamino, hydrazino, trifluoromethyl, trifluoromethoxy, alkenyl, alkynyl, aryl and heterocyclic; and $R_2$ and $R_3$ are substituent groups of —$(CH_2)_m$—$R_4$ and may be identical or different, wherein m is 0 or 1, and wherein $R_4$ is selected from the group consisting of hydrogen, halogen, $C_{1-6}$-alkyl, $C_{3-6}$-cycloalkyl, hydroxy, $C_{1-6}$-alkoxy, $C_{3-6}$-cycloalkoxy, $C_{1-6}$-thioalkoxy, $C_{3-6}$-thiocycloalkoxy, amino, mono($C_{1-6}$)-alkylamino, di($C_{1-6}$)-alkylamino, formamido, nitro, hydroxyamino, $C_{1-6}$-alkoxyamino, hydrazino, cyano, carboxyl, alkoxycarbonyl, amido, N-monoalkyl($C_{1-6}$)-amido, N,N-dialkyl ($C_{1-6}$)-amido, thioamido, N-monoalkyl ($C_{1-6}$)-thioamido, N,N-dialkyl($C_{1-6}$)-thioamido, guanidino, ureido, $C_{1-6}$-alkylsulfido, $C_{1-6}$-alkylsulfonyl, trifluoromethyl, trifluoromethoxy, morpholino, 4-$C_{1-6}$-alkylpiperidino, mono[hydroxy($C_{1-6}$)alkyl]amino, di[hydroxy($C_{1-6}$)alkyl]amino, mono[pyrrolidine($C_{1-6}$)alkyl]

amino, and di[pyrrolidine($C_{1-6}$)alkyl]amino or —$N(R_5)$ ($CHR_6R_7$), wherein $R_5$ is hydrogen or $C_{1-6}$-alkyl, $R_6$ is $(CH_2)_nOH$ where n is an integer of 1 to 4, and $R_7$ is selected from the group consisting of hydrogen, $C_{1-5}$-alkyl, hydroxy($C_{1-5}$)-alkyl, thiohydroxy($C_{1-5}$)-alkyl, phenyl($C_{1-5}$)-alkyl, 4-hydroxyphenyl($C_{1-5}$)-alkyl and heteroallyl($C_{1-5}$)-alkyl.

In the above-discussed compound, or a pharmaceutically acceptable salt, hydrate or solvate thereof, the pharmaceutically acceptable salt comprises an inorganic acid salt, an organic acid salt or a sulfonic acid salt of the compound. The he inorganic acid salt is one or more selected from the group consisting of a hydrochloric acid salt, a hydrobromic acid salt, a hydroiodic acid salt, a sulfuric acid salt, a nitric acid salt and a phosphoric acid salt. The organic acid salt is one or more selected from the group consisting of an acetic acid salt, a succinic acid salt, a tartaric acid salt, a malic acid salt, a formic acid salt, a citric acid salt, a trichloroacetic acid salt, a trifluoroacetic acid salt, a gluconic acid salt, a lactic acid salt, a fumaric acid salt, a picric acid salt and a maleic acid salt. The sulfonic acid salt is one or more selected from the group consisting of a methane sulfonic acid salt, a benzene sulfonic acid salt, a p-toluene sulfonic acid salt and a naphthalene sulfonic acid salt. The above-discussed compound, or a pharmaceutically acceptable salt, hydrate or solvate thereof, is selected from the group consisting of: (3-bromophenyl)-(7-methoxymethyl-[1,4]-dioxano[2,3-g]quinazolin-4-yl)-amine, (3,5-dichlorophenyl)-(7-methoxymethyl-[1,4]-dioxano[2,3-g]quinazolin-4-yl)-amine, (3,5-dimethylphenyl)-(7-methoxymethyl-[1,4]-dioxano[2,3-g]quinazolin-4-yl)-amine, (3,4,5-trifluorophenyl)-(7-methoxymethyl-[1,4]-dioxano[2,3-g]quinazolin-4-yl)-amine, (3-iodophenyl)-[7-(morpholin-4-yl-methyl)-[1,4]dioxano[2,3-g]quinazolin-4-yl]-amine, (3-bromophenyl)-[7-(morpholin-4-yl-methyl)-[1,4]dioxano[2,3-g]quinazolin-4-yl]-amine, (3-bromophenyl)-[7-(morpholin-4-yl-methyl)-[1,4]dioxano[2,3-g]quinazolin-4-yl]-amine hydrochloride, 2-[4-(3-bromophenylamine)-[1,4]dioxano[2,3-g]quinazolin-7-yl-methyl]-aminoethanol, and (3-bromophenyl)-[7-(4-methylpiperazin-1-yl) methyl-[1,4]dioxano[2,3-g] quinazolin-4-yl]-amine.

Another aspect of the present invention provides a process for preparing the above-discussed compound, or a pharmaceutically acceptable salt, hydrate or solvate thereof, the process comprising: providing a quinazoline derivative of Formula (II) and a substituted aniline of Formula (III):

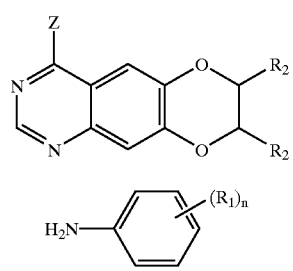

Formula (II)

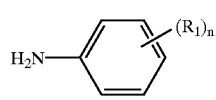

Formula (III)

wherein Z is halogen, alkoxy, aryloxy or sulfonyloxy; mixing the quinazoline derivative and the substituted aniline in the presence of an organic solvent to provide a liquid mixture; and adding an acid to the liquid mixture, thereby forming the compound, or a pharmaceutically acceptable salt, hydrate or solvate thereof In the mixing 1 equi. of the quinazoline derivative and 2 equi. of the substituted aniline are mixed together. The organic solvent is an inert organic solvent. The organic solvent is selected from the group consisting of an alkanol, an ester, a halogenated solvent, an ether, an aromatic solvent, N,N-dimethylformamide, and mixtures of the foregoing. The added acid is hydrochloric acid. The process further comprises maintaining the mixture after the addition of the acid at a temperature from about 20° C. to about 80° C.

Another aspect of the present invention provides a pharmaceutical composition comprising a pharmaceutical carrier and the above-discussed compound, or a pharmaceutically acceptable salt, hydrate or solvate thereof.

Still another aspect of the present invention provides a method of regulating activities of tyrosine kinase, comprising administering to a patient in need of such regulation a composition comprising a pharmaceutically acceptable carrier and a pharmaceutically effective amount of the above-discussed compound, or a pharmaceutically acceptable salt, hydrate or solvate thereof.

A further aspect of the present invention provides a method of inhibiting cancer cell growth, comprising administering to a patient in need of such inhibition a composition comprising a pharmaceutically acceptable carrier and a pharmaceutically effective amount of the above-discussed compound, or a pharmaceutically acceptable salt, hydrate or solvate thereof.

In the methods of regulating activities of tyrosine kinase and inhibiting cancer cell growth, the compound, or a pharmaceutically acceptable salt, hydrate or solvate thereof, is selected from the group consisting of: (3-bromophenyl)-(7-methoxymethyl-[1,4]-dioxano[2,3-g]quinazolin-4-yl)-amine, (3,5-dichlorophenyl)-(7-methoxymethyl-[1,4]-dioxano[2,3-g]quinazolin-4-yl)-amine, (3,5-dimethylphenyl)-(7-methoxymethyl-[1,4]-dioxano[2,3-g]quinazolin-4-yl)-amine, (3,4,5-trifluorophenyl)-(7-methoxymethyl-[1,4]-dioxano[2,3-g]quinazolin-4-yl)-amine, (3-iodophenyl)-[7-(morpholin-4-yl-methyl)-[1,4]dioxano[2,3-g]quinazolin-4-yl]-amine, (3-bromophenyl)-[7-(morpholin-4-yl-methyl)-[1,4]dioxano[2,3-g]quinazolin-4-yl]-amine, (3-bromophenyl)-[7-(morpholin-4-yl-methyl)-[1,4]dioxano[2,3-g]quinazolin-4-yl]-amine hydrochloride, 2-[4-(3-bromophenylamine)-[1,4]dioxano[2,3-g]quinazolin-7-yl-methyl]-aminoethanol, and (3-bromophenyl)-[7-(4-methylpiperazin-1-yl) methyl-[1,4]dioxano[2,3-g]quinazolin-4-yl]-amine. In the method, the pharmaceutically acceptable salt comprises an inorganic acid salt, organic acid salt or sulfonic acid salt of the compound.

DETAILED DESCRIPTION OF THE INVENTION

The present invention provides 4-(phenylamino)-[1,4]dioxano[2,3-g]quinazoline derivatives which inhibit the activity of tyrosine kinase of EGFR, represented as the following general formula(I), and pharmaceutically acceptable salts, hydrates and solvates thereof, and a process for preparing the same.

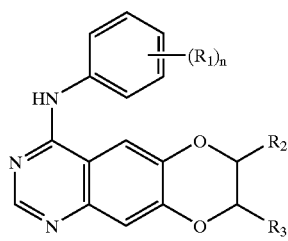

(I)

Here, $R_1$ is hydrogen, halogen, $C_{1-6}$-alkyl, $C_{3-6}$-cycloalkyl, hydroxy, $C_{1-6}$-alkoxy, $C_{3-6}$-cycloalkoxy, (aryl or heteroaryl)oxy, $C_{1-6}$-thioalkoxy, $C_{3-6}$-thiocycloalkoxy, thio (aryl or heteroaryl)oxy, nitro, amino, N-mono($C_{1-6}$)-alkylamino, N,N-di($C_{1-6}$)-alkylamino, formamido, amido, acetamido, hydroxyamino, $C_{1-6}$-alkoxyamino, hydrazino, trifluoromethyl, trifluoromethoxy, alkenyl, alkynyl, aryl or heterocyclic; $R_2$ and $R_3$, which may be the same or different, are —($CH_2$)m—$R_4$[where, m is 0 or 1; $R_4$ is hydrogen, halogen, $C_{1-6}$-alkyl, $C_{3-6}$-cycloalkyl, hydroxy, $C_{1-6}$-alkoxy, $C_{3-6}$-cycloalkoxy, $C_{1-6}$-thioalkoxy, $C_{3-6}$-thiocycloalkoxy, amino, mono($C_{1-6}$)-alkylamino, di($C_{1-6}$)-alkylamino, formamido, nitro, hydroxyamino, $C_{1-6}$-alkoxyamino, hydrazino, cyano, carboxyl, alkoxycarbonyl, amido, N-monoalkyl($C_{1-6}$)-amido, N,N-dialkyl ($C_{1-6}$)-amido, thioamido, N-monoalkyl($C_{1-6}$)-thioamido, N,N-dialkyl($C_{1-6}$)-thioamido, guanidino, ureido, $C_{1-6}$-alkylsulfido, $C_{1-6}$-alkylsulfonyl, trifluoromethyl, trifluoromethoxy, morpholino, 4-$C_{1-6}$-alkylpiperidino, mono[hydroxy($C_{1-6}$)alkYl]amino, di[hydroxy($C_{1-6}$)alkyl]amino, mono[pyrrolidine($C_{1-6}$)alkyl]amino, di[pyrrolidine($C_{1-6}$)alkyl]amino or —N($R_5$)($CHR_7$) {where, $R_5$ is hydrogen or $C_{1-6}$-alkyl; $R_6$ is ($CH_2$)$_n$OH(where, n is an integer of 1 to 4); and, $R_7$ is hydrogen, $C_{1-5}$-alkyl, hydroxy($C_{1-5}$)-alkyl, thiohydroxy($C_{1-5}$)-alkyl, phenyl($C_{1-5}$)-alkyl, 4-hydroxyphenyl($C_{1-5}$)-alkyl or heteroallyl($C_{1-5}$)-alkyl}]; and n is 1, 2 or 3.

The pharmaceutically acceptable nontoxic salts of the compound represented as the general formula(I) include inorganic acid salts prepared with inorganic acids such as hydrochloric acid, hydrobromic acid, hydroiodic acid, sulfuric acid, nitric acid, phosphoric acid; organic acid salts prepared with organic acids such as acetic acid, succinic acid, tartaric acid, malic acid, formic acid, citric acid, trichloroacetic acid, trifluoroacetic acid, gluconic acid, lactic acid, fumaric acid, picric acid, maleic acid; sulfonic acid salts prepared with sulfonic acids such as methane sulfonic acid, benzene sulfonic acid, p-toluene sulfonic acid, naphthalene sulfonic acid, and the compound represented as the general formula(I) may be in a form of hydrate or solvate.

4-(phenylamino)-[1,4]dioxano[2,3-g]quinazoline derivatives of the invention preferably include the followings: (7-methoxymethyl-[1,4]dioxano[2,3-g]quinazolin-4-yl)-phenyl-amine; (7-methoxymethyl-[1,4]dioxano[2,3-g]quinazolin-4-yl)-(3-chlorophenyl)-amine; (7-methoxymethyl-[1,4]dioxano[2,3-g]quinazolin-4-yl)-phenyl-(3-bromophenyl)-amine; (7-methoxymethyl-[1,4]dioxano[2,3-g]quinazolin-4-yl)-(3-iodophenyl)-amine; (7-methoxymethyl-[1,4]dioxano[2,3-g]quinazolin-4-yl)-(3-fluorophenyl)-amine; (7-methoxymethyl-[1,4]dioxano[2,3-g]quinazolin-4-yl)-(3-fluoro-4-chlorophenyl)-amine; (7-methoxymethyl-[1,4]dioxano[2,3-g]quinazolin-4-yl)-(3,5-dimethylphenyl)-amine; (7-methoxymethyl-[1,4]dioxano[2,3-g]quinazolin-4-yl)-(3,4-dichlorophenyl)-amine; (7-methoxymethyl-[1,4]dioxano[2,3-g]quinazolin-4-yl)-(3,4,5-trifluorophenyl)-amine; (7-morpholin-4-ylmethyl-[1,4]dioxano[2,3-g]quinazolin-4-yl)-(3-bromophenyl)-amine; (7-morpholin-4-ylmethyl-[1,4]dioxano[2,3-g] quinazolin-4-yl)-(3-iodophenyl)-amine; (7-bis(2-hydroxyethyl)aminomethyl-[1,4]dioxano[2,3-g]quinazolin-4-yl)-(3-bromophenyl)-amine; (7-bis(2-hydroxyethyl)aminomethyl-[1,4]dioxano[2,3-g]quinazolin-4-yl)-(3-iodophenyl)-amine; (7-(2-hydroxyethyl)aminomethyl-[1,4]dioxano[2,3-g]quinazolin-4-yl)-(3-bromophenyl)-amine; (7-(2-hydroxyethyl)aminomethyl-[1,4]dioxano[2,3-g]quinazolin-4-yl)-(3-iodophenyl)-amine; (7-(4-methylpiperazin-1-ylmethyl-[1,4]dioxano[2,3-g]quinazolin-4-yl)-(3-bromophenyl)-amine; (7-(2-hydroxy-1-isopropylethyl)aminomethyl-[1,4]dioxano[2,3-g]quinazoline-4-amine; (7-(2-pyrrolidine-1-ethyl)aminomethyl-[1,4]dioxano[2,3-g]quinazolin-4-yl)-phenyl-amine; (7,8-dimethoxymethyl-[1,4]dioxano[2,3-g]quinazolin-4-yl)-(3-bromophenyl)-amine; (7,8-dimethoxymethyl-[1,4]dioxano[2,3-g]quinazolin-4-yl)-(3-chlorophenyl)-amine; (7,8-dimethoxymethyl-[1,4]dioxano[2,3-g]quinazolin-4-yl)-(3-iodophenyl)-amine; and, (7,8-dimethoxymethyl-[1,4]dioxano[2,3-g]quinazolin-4-yl)-(3-ethinylphenyl)-amine and hydrochloride thereof.

The said 4-(phenylamino)-[1,4]dioxano[2,3-g]quinazoline derivatives represented as the general formula (I) is prepared by mixing 1 equi. of quinazoline derivative of the general formula(II) and 2 equi. of substituted aniline of the general formula(III) in the presence of an inert organic solvent, adding hydrochloric acid, and reacting the resulting mixture at 20 to 80° C.: where the inert organic solvent includes alkanol, ester, halogenated solvent, ether, aromatic solvent, N,N-dimethylformamide, etc., preferably, isopropanol. Also, in case of employing quinazoline derivatives of the general formula(II) with chiral carbons, optically active quinazoline derivatives of the general formula(I) are prepared.

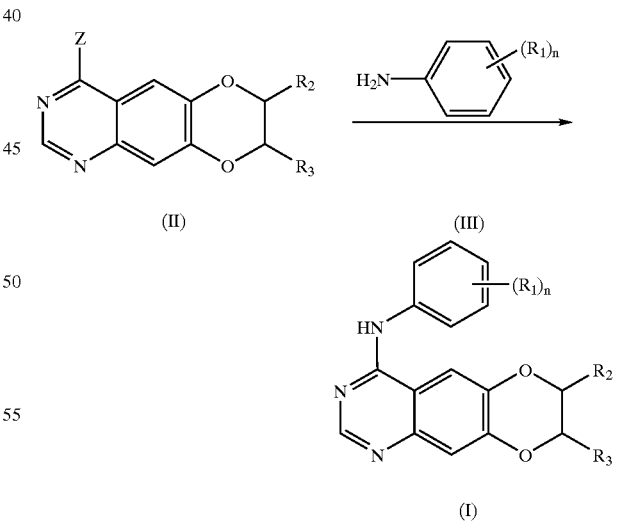

wherein $R_1$, $R_2$ and $R_3$ are the same as defined in the general formula(I); and Z is halogen, alkoxy, aryloxy or sulfonyloxy.

The present invention is further illustrated in the following examples, which should not be taken to limit the scope of the invention.

EXAMPLE 1
Preparation of 2-methoxymethyl-benzo-1,4-dioxane

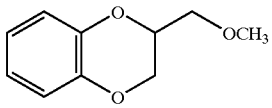

THF (60 ml) was added slowly to NaH (5.02 g, 0.209 mol) at 0° C. in the presence of nitrogen and stirred for 20 min, and then, 2-hydromethyl-benzo-1,4-dioxane (28.89 g, 0.174 mol) was added slowly, followed by stirring for 30 min at a room temperature. Then, iodomethane (16.25 ml, 0.261 mol) was added to the reaction mixture, stirred for 48 hours and extracted with ethylacetate, followed by removing the solvent. The resultant was dried to prepare the titled compound (24 g, 78%).

$^1$H NMR(300 MHz, CDCl$_3$): δ 6.96–6.89 (m, 4H), 4.28 (m, 1H), 4.08–4.04 (m, 2H), 3.69–3.57 (m, 2H), 3.41 (s, 3H)

EXAMPLE 2
Preparation of (3-methoxymethyl-benzo-1,4-dioxan-6-yl) methyl ketone

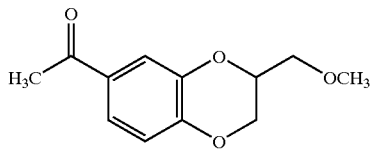

Dimethyl acetamide (16.65 mol, 1.31 ml) was added slowly to anhydrous aluminum chloride (33.3 mmol, 4.44 g) at 0° C. in the presence of nitrogen and stirred for 30 min at a room temperature, and then, the titled compound prepared in Example 1 (3.77 mmol, 500 mg) was added slowly to the resulting mixture, followed by stirring for 15 min. Then, acetyl chloride (3.33 mmol, 0.28 ml) was added and stirred for 5 hours at a room temperature. Ice was added slowly to the mixture to destroy and remove the remaining aluminum chloride. The reaction mixture was neutralized with NaHCO$_3$, extracted with ethylacetate, followed by removing the solvent. And then, the resultant was dried to prepare the titled compound (520 mg, 84%).

$^1$H NMR(300 MHz, CDCl$_3$): δ 7.53–7.47 (m, 2H), 6.94–6.83 (m, 2H), 4.33 (m, 1H), 4.12–4.11 (m, 2H), 3.67–3.57 (m, 2H), 3.42 (s, 3H), 2.51 (s, 3H)

EXAMPLE 3
Preparation of 3-methoxymethyl-benzo-1,4-dioxan-6-carboxylic acid

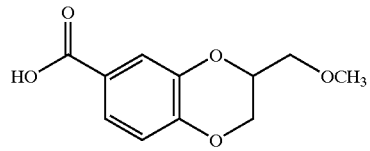

To 13% (v/v) NaOCl (140 ml, purchased from Fluka) solution was added the titled compound of Example 2 (12.85 g, 0.0578 mol), followed by stirring. After being refluxed for 30 min while maintaining the temperature of 65° C., the reaction mixture was cooled down to a room temperature, stirred for 30 min and filtered to obtain a filtrate. To the said filtrate was added 10 ml of 25% (w/v) sodium hydrosulfide, and then, concentrated hydrochloric acid was added to adjust the pH by 3–4. The reaction mixture was filtered to give a solid, which was then washed and recrystallized with a mixture of water and ethanol (40:60, v/v) to prepare the titled compound (6.262 g, 48%, m.p. 119–123° C.).

$^1$H NMR(300 MHz, CD$_3$OD): δ 7.53–7.49 (m, 2H), 6.91–6.89 (m, 1H), 4.39–4.31 (m, 2H), 4.07 (m, 1H), 3.67–3.61 (m, 2H), 3.40 (s, 3H)

EXAMPLE 4
Preparation of 3-methoxymethyl-7-nitro-benzo-1,4-dioxane-6-carboxylic acid

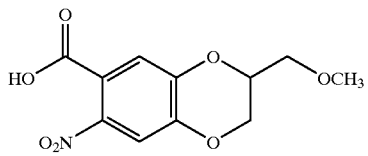

The titled compound of Example 3 (0.788 g, 3.51 mmol) was dissolved in 2 ml of acetic acid, and added a mixture of nitric acid (3 ml) and sulfuric acid (3 ml), followed by stirring for 30 min. Then, to the reaction mixture was added 10 ml of water to give a solid, which was then fitered and washed with acetic acid and ether in a sequential order to prepare the titled compound (0.510 g, 54%).

$^1$H NMR(300 MHz, CDCl$_3$): δ 7.41 (s, 1H), 7.33 (m, 1H), 4.52–4.51 (m, 2H), 4.40 (m, 1H), 3.70–3.61 (m, 2H), 3.44 (s, 3H)

EXAMPLE 5
Preparation of 7-amino-3-methoxymethyl-benzo-1,4-dioxane-6-carboxylic acid

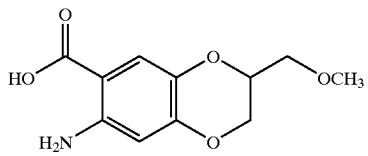

The titled compound of Example 4 (1.22 g, 4.53 mmol) was dissolved in 10 ml of methanol, and added 10% (w/v) Pd/C as a catalyst, followed by stirring for 24 hours at 25° C. Then, the reaction mixture was filtered to give a filtrate, which was then dried under vacuum to obtain a solid compound. The solid compound was recrystallized with ethanol to prepare the titled compound (0.702 g, 65%, m.p. 161–167° C.).

$^1$H NMR(300 MHz, CDCl$_3$): δ 7.49 (s, 1H), 6.17 (s, 2H), 4.34–4.24 (m, 2H), 4.12 (m, 1H), 3.67–3.59 (m, 2H), 3.44 (s, 3H)

EXAMPLE 6
Preparation of 7-methoxy-[1,4]dioxano[2,3-g]quinazolin-4-ol

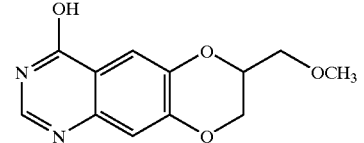

The titled compound of Example 5 (0.367 g, 1.53 mmol), triazine (0.19 g, 2.3 mmol) and piperidine (0.015 ml, 0.153 mmol) was dissolved in 10 ml of methanol, followed by refluxing for 4 hours to obtain a white solid, which was then cooled down to a room temperature. The solid compound was filtered, washed with methanol and dried under vacuum to prepare the titled compound (0.240 g, 63%, m.p. 246–251° C.).

$^1$H NMR(300 MHz, DMSO-d6): δ 7.92 (s, 1H), 7.46 (s, 1H), 7.09 (s, 2H), 4.46–4.19 (m, 2H), 4.13 (m, 1H), 3.62–3.60 (m, 2H), 3.32 (s, 3H)

EXAMPLE 7

Preparation of 4-chloro-7-methoxymethyl-[1,4]dioxano[2,3-g]quinazoline

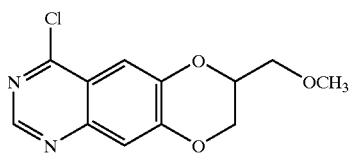

The titled compound of Example 6 (0.5 g, 2 mmol) was dissolved in POCl$_3$ (25 ml), followed by refluxing with N,N-dimethylaniline (0.636 ml, 5.486 mmol) for 2 hours and removing the solvent under a reduced pressure to obtain a solid compound, which was then dissolved in dichloromethane. The dichloromethane solution was poured into ice water and then, a product was extracted with dichloromethane. The extract solution was neutralized with NaHCO$_3$ aqueous solution and dried over MgSO$_4$ to prepare the titled compound (0.5 g, 90%).

$^1$H NMR(300 MHz, DMSO-d6): δ 8.88 (s, 1H), 7.61 (s, 1H), 7.50 (s, 2H), 4.59–4.55 (m, 2H), 4.26 (m, 1H), 3.67–3.66 (m, 2H), 3.25 (s, 3H)

EXAMPLE 8

Preparation of (3-fluorophenyl)-(7-methoxymethyl-[1,4]-dioxano[2,3-g]quinazolin-4-yl)-amine

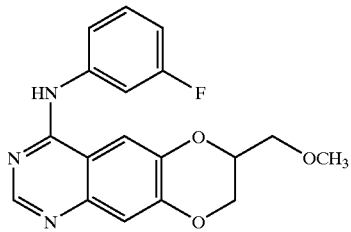

The titled compound of Example 7, 4-chloro-7-methoxy methyl-[1,4]dioxano[2,3-g]quinazoline (40 mg, 0.15 mmol) was dissolved in diisopropanol (2.5 ml), where was then added 3-fluoroaniline (33 mg, 0.3 mol) and concentrated hydrochloric acid of catalytic amount, followed by refluxing for 24 hours. Then, the reaction mixture was cooled down to a room temperature to obtain a solid, which was then filtered, washed with diisopropanol and dried under vacuum to prepare the titled compound (24 mg, 47%, m.p. 257–260° C.; mass (m/z;rel) 340.10).

$^1$H NMR(300 MHz, DMSO-d6): δ 11.16 (s, 1H), 8.90 (s, 1H), 8.47 (s, 1H), 7.76 (m, 1H), 7.62–7.51 (m, 2H), 7.41 (s, 1H), 7.15 (m, 1H), 4.63–4.58 (m, 2H), 4.30 (m, 1H), 3.67 (d, J=4.5 Hz, 2H), 3.35 (s, 3H)

EXAMPLE 9

Preparation of (3-chlorophenyl)-(7-methoxymethyl-[1,4]-dioxano[2,3-g]quinazolin-4-yl)-amine

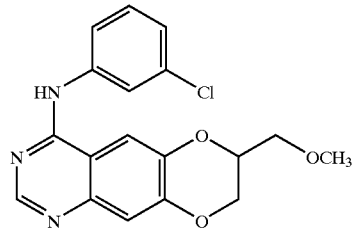

The titled compound (25 mg, 63%, m.p. 277–282° C.) was prepared in a similar manner as in Example 8, except for employing 4-chloro-7-methoxymethyl-[1,4]dioxano[2,3-g]quinazoline (30 mg, 0.113 mmol) and 3-chloroaniline (28 mg, 0.226 mmol).

$^1$H NMR(300 MHz, DMSO-d6): δ 10.89 (s, 1H), 8.87 (s, 1H), 8.87 (s, 1H), 7.97 (m, 1H), 7.73 (m, 1H), 7.51 (m, 1H), 7.37 (m, 1H), 7.34 (s, 1H), 4.62–4.57 (m, 2H), 4.29 (m, 1H), 3.68 (d, J=4.5 Hz, 2H), 3.35 (s, 3H)

EXAMPLE 10

Preparation of (3-bromophenyl)-(7-methoxymethyl-[1,4]-dioxano[2,3-g]quinazolin-4-yl)-amine

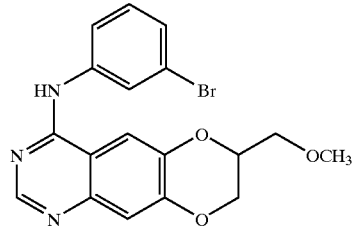

The titled compound (25 mg, 63%, m.p. 268–274° C.) was prepared in a similar manner as in Example 8, except for employing 4-chloro-7-methoxymethyl-[1,4]dioxano[2,3-g]quinazoline (30 mg, 0.113 mmol) and 3-bromoaniline (39 mg, 0.226 mmol).

$^1$H NMR(300 MHz, DMSO-d6): δ 10.80 (s, 1H), 9.10 (s, 1H), 8.41 (s, 1H), 8.08 (m, 1H), 7.62 (m, 1H), 7.49 (m, 1H), 7.37 (m, 1H), 7.30 (s, 1H), 4.62–4.58 (m, 2H), 4.30 (m, 1H), 3.68 (d, J=4.5 Hz, 2H), 3.34 (s, 3H)

EXAMPLE 11

Preparation of (3-iodophenyl)-(7-methoxymethyl-[1,4]-dioxano[2,3-g]quinazolin-4-yl)-amine

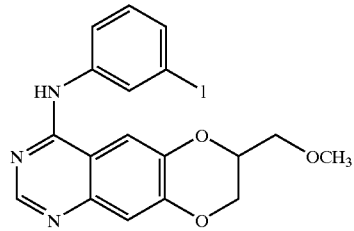

The titled compound (260 mg, 94%, m.p. 175–177° C.) was prepared in a similar manner as in Example 8, except for employing 4-chloro-7-methoxymethyl-[1,4]dioxano[2,3-g]quinazoline (175 mg, 0.8 mmol) and 3-iodoaniline (350 mg, 1.6 mmol).

¹H NMR(300 MHz, DMSO-d6): δ 10.70 (s, 1H), 9.19 (s, 1H), 8.31 (s, 1H), 8.21 (s, 1H), 7.80 (m, 1H), 7.64 (m, 1H), 7.30 (s, 1H), 7.26 (m, 1H), 4.60–4.57 (m, 2H), 4.28 (m, 1H), 3.68 (d, J=4.5 Hz, 2H), 3.34 (s, 3H)

EXAMPLE 12

Preparation of (3-trifluoromethylphenyl)-(7-methoxymethyl-[1,4]-dioxano[2,3-g]quinazolin-4-yl)-amine

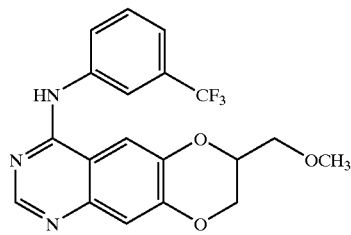

The titled compound (28 mg, 80%, m.p. 280–282° C.) was prepared in a similar manner as in Example 8, except for employing 4-chloro-7-methoxymethyl-[1,4]dioxano[2,3-g]quinazoline (24 mg, 0.09 mmol) and 3-trifluoroaniline (29 mg, 0.18 mmol).

¹H NMR(300 MHz, DMSO-d6): δ11.11 (s, 1H) 8.90 (s, 1H), 8.41 (s, 1H), 8.21 (s, 1H), 8.10 (d, J=8.1 Hz, 1H), 7.75–7.64 (m, 2H), 7.37 (s, 1H), 4.65–4.58 (m, 2H), 4.35–4.26 (m, 1H), 3.68 (d, J=4.5 Hz, 2H), 3.35 (s, 3H)

EXAMPLE 13

Preparation of (3,5-dichlorophenyl)-(7-methoxymethyl-[1,4]-dioxano[2,3-g]quinazolin-4-yl)-amine

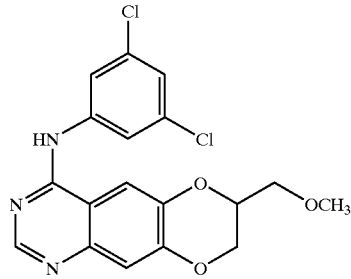

The titled compound (20 mg, 80%, m.p. 269–274° C.) was prepared in a similar manner as in Example 8, except for employing 4-chloro-7-methoxymethyl-[1,4]dioxano[2,3-g]quinazoline (17 mg, 0.06 mmol) and 3,5-dichloroaniline (21 mg, 0.12 mmol).

¹H NMR(300 MHz, DMSO-d6): δ 10.89 (s, 1H), 8.90 (S, 1H), 8.36 (s, 1H), 7.96–7.93 (m, 2H), 7.49 (s, 1H), 7.34 (s, 1H), 4.59–4.55 (m, 2H), 4.27 (m, 1H), 3.66 (d, J=4.5 Hz, 2H), 3.32 (s, 3H)

EXAMPLE 14

Preparation of [3,5-bis(trifluoromethyl) phenyl]-(7-methoxymethyl-[1,4]-dioxano[2,3-g]quinazolin-4-yl)-amine

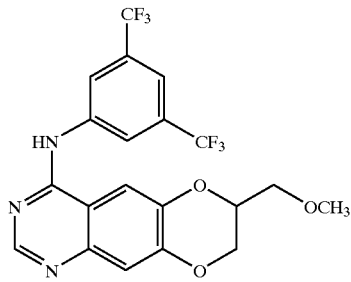

The titled compound (8 mg, 50%) was prepared in a similar manner as in Example 8, except for employing 4-chloro-7-methoxymethyl-[1,4]dioxano[2,3-g]quinazoline (10 mg, 0.037 mmol) and 3,5-bis(trifluoromethyl)aniline (17 mg, 0.075 mmol).

¹H NMR(300 MHz, DMSO-d6): δ 10.35 (s, 1H), 8.73 (m, 3H), 8.24 (s, 1H), 7.84 (s, 1H), 7.30 (s 1H), 4.61–4.54 (m, 2H), 4.27–4.21 (m, 1H), 3.68 (d, J=4.5 Hz, 2H), 3.16 (s, 3H)

EXAMPLE 15

Preparation of (3,5-dimethylphenyl)-(7-methoxymethyl-[1,4]-dioxano[2,3-g]quinazolin-4-yl)-amine

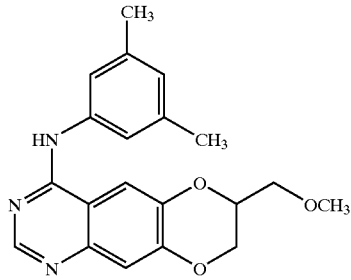

The titled compound (10 mg, 29%, m.p. 268–270° C.) was prepared in a similar manner as in Example 8, except for employing 4-chloro-7-methoxymethyl-[1,4]dioxano[2,3-g]quinazoline (26 mg, 0.1 mmol) and 3,5-dimethylaniline (24 mg, 0.2 mmol).

¹H NMR(300 MHz, DMSO-d6): δ 8.75 (s, 1H), 8.32 (s, 1H), 7.34 (s, 1H), 7.30 (s, 2H), 6.93 (s, 1H), 4.59–4.55 (m, 2H), 4.27 (m, 1H), 3.67 (d, J=4.5 Hz, 2H), 3.16 (s, 3H), 2.31 (s, 6H)

EXAMPLE 16

Preparation of (3-chloro-4-methylphenyl)-(7-methoxymethyl-[1,4]-dioxano[2,3-g]quinazolin-4-yl)-amine

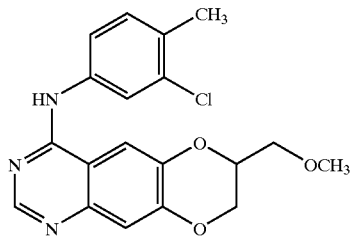

The titled compound (54 mg, 49%) was prepared in a similar manner as in Example 8, except for employing 4-chloro-7-methoxymethyl-[1,4]dioxano[2,3-g]quinazoline (80 mg, 0.3 mmol) and 3-chloro-4-methylaniline (84 mg, 0.6 mmol).

$^1$H NMR(300 MHz, DMSO-d6): δ 11.11 (s, 1H), 8.88 (s, 1H), 8.42 (s, 1H), 7.90 (s, 1H), 7.61 (m, 1H), 7.43 (m, 1H), 7.38 (s, 1H), 4.62–4.54 (m, 2H), 4.26 (m, 1H), 3.68 (d, J=4.5 Hz, 2H), 3.35 (s, 3H), 2.36 (s, 3H)

EXAMPLE 17

Preparation of (3-chloro-4-fluorophenyl)-(7-methoxymethyl-[1,4]-dioxano[2,3-g]quinazolin-4-yl)-amine

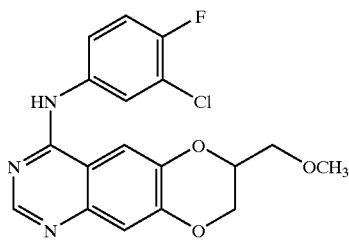

The titled compound (11 mg, 26%, m.p. 260–285° C.) was prepared in a similar manner as in Example 8, except for employing 4-chloro-7-methoxymethyl-[1,4]dioxano[2,3-g]quinazoline (30 mg, 0.11 mmol) and 3-chloro-4-methylaniline (31 mg, 0.22 mmol).

$^1$H NMR(300 MHz, DMSO-d6): δ 11.12 (s, 1H), 8.92 (s, 1H), 8.48 (s, 1H), 8.17 (m, 1H), 7.83 (s, 1H), 7.61 (s, 1H), 7.45 (s, 1H), 4.68–4.65 (m, 2H), 4.36 (m, 1H), 3.83 (d, J=6.3 Hz, 2H), 3.42 (s, 3H)

EXAMPLE 18

Preparation of (3,4,5-trifluorophenyl)-(7-methoxymethyl-[1,4]-ioxano[2,3-g]quinazolin-4-yl)-amine

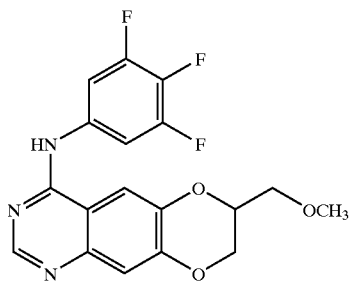

The titled compound (32 mg, 65%, m.p. 285–290° C.) was prepared in a similar manner as in Example 8, except for employing 4-chloro-7-methoxymethyl-[1,4]dioxano[2,3-g]quinazoline (35 mg, 0.14 mmol) and 3,4,5-trifluoroaniline (41 mg, 0.28 mmol).

$^1$H NMR(300 MHz, DMSO-d6): δ 10.9 (s, 1H), 8.87 (s, 1H), 8.33 (s, 1H), 7.89–7.84 (m, 2H), 7.35 (s 1H), 4.61–4.57 (m, 2H), 4.28 (m, 1H), 3.68 (d, J=4.7 Hz, 2H), 3.42 (s, 3H)

EXAMPLE 19

Preparation of (4-(3-iodophenyl [1,4]-dioxano[2,3-g]quinazolin-4-yl)-amine

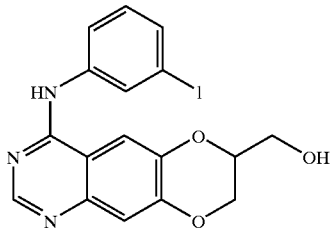

The titled compound of Example 11, (3-iodophenyl)-(7-methoxymethyl-[1,4]-dioxano[2,3-g]quinazolin-4-yl)-amine (400 mg, 0.863 mmol) was dissolved in dichloromethane (10 ml), and then added slowly tribromoborane (3.9 ml, 3.45 mmol) dissolved in 1M hexane in the presence of nitrogen of −78° C. Then, the reaction mixture was stirred at −78° C. for 1 hour and at a room temperature for 24 hours once more. After that, NaHCO$_3$ aqueous solution was added to the mixture and, the product was extracted with ethylacetate and dried over MgSO$_4$ to prepare the titled compound (301 mg, 78%).

$^1$H NMR(300 MHz, CD$_3$OD): δ 8.42 (s, 1H), 8.10 (s, 1H), 7.87 (s, 1H), 7.70 (m, 1H), 7.29–7.21 (m, 3H), 4.49 (m, 1H), 4.35 (m, 1H), 4.29 (m, 1H), 3.86 (d, J=4.8 Hz, 2H), 3.42 (s, 3H)

EXAMPLE 20

Preparation of [4-(3-iodophenylamine)-[1,4]-dioxano[2,3-g]quinazolin-7-yl]methylmethanesulfonate

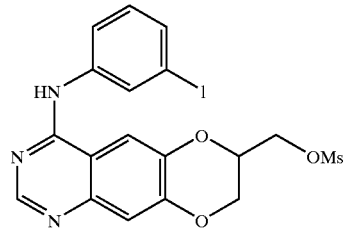

The titled compound of Example 19 (960 mg, 2.47 mmol) was dissolved in dichloromethane (5 ml), which was then mixed with triethylamine (0.688 ml, 4.94 mmol) in the presence of nitrogen of 0° C. Then, methanesulfonyl chloride (0.382 ml, 4.94 mmol) was added slowly to the reaction mixture, followed by stirring for 1 hour and then, at a room temperature for 24 hours once more. After that, NaHCO$_3$ aqueous solution was added to the mixture and, the product was extracted with ethylacetate and dried over MgSO$_4$ to remove the solvent. The obtained residue was purified by a column chromatography (mobile phase: ethylacetate:hexane=2:1 (v:v)) to prepare a pure titled compound (900 mg, 78%).

$^1$H NMR(300 MHz, CDCl$_3$): δ 8.69 (s, 1H), 8.19 (s, 1H), 8.02 (s, 1H), 7.75 (d, J=8.3 Hz, 1H), 7.49 (d, J=8.7 Hz, 1H), 7.43 (s, 1H), 7.12 (t, J=8.0 Hz, 1H), 4.62–4.44 (m, 4H), 4.25 (m, 1H), 3.13 (s, 3H)

EXAMPLE 21
Preparation of [4-(3-bromophenylamine)-[1,4]-dioxano[2,3-g]quinazolin-7-yl]methylmethanesulfonate

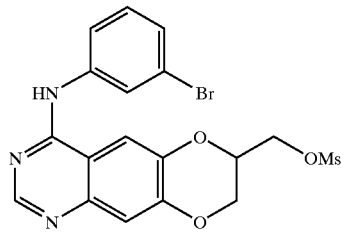

The titled compound (900 mg, 78%) was prepared in a similar manner as in Examples 19 and 20, except for employing the titled compound of Example 10 (960 mg, 2.47 mmol).

$^1$H NMR(300 MHz, CDCl$_3$): δ 8.42 (s, 1H), 8.10 (s, 1H), 7.91 (s, 1H), 7.70 (m, 1H), 7.28–7.27 (m, 2H), 7.21 (s, 1H), 4.65 (m, 1H), 4.60–4.55 (m, 4H), 3.1 (s, 3H)

EXAMPLE 22
Preparation of (3-iodophenyl)-[7-(morpholine-4-ylmethyl)-[1,4]dioxano[2,3-g]quinazolin-4-yl]-amine

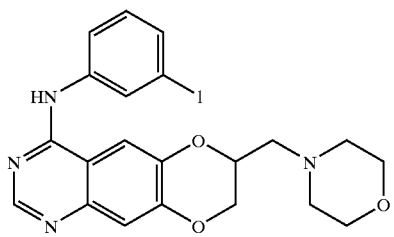

The titled compound of Example 20 (140 mg, 0.272 mmol) was dissolved in THF (3 ml), and then added morpholine (35 mg, 0.41 mmol) and triethylamine (41 mg, 0.41 mmol), followed by heating for 3 hours. The solvent was removed from the reaction mixture to obtain a solid, which was then washed with water, NaCl solution and ethylacetate in a sequential order to remove excess base. The resulting residue was purified by a column chromatography to prepare a pure titled compound (60 mg, 44%, m.p. 238–240° C.).

IR(KBr): 2966, 2806, 1512, 1424, 1274, 1228 cm$^{-1}$ $^1$H NMR(300 MHz, CD$_3$OD): δ 8.41 (s, 1H), 8.25 (s, 1H) 7.86 (s, 1H) 7.76 (d, J=8.3 Hz, 1H), 7.48 (d, J=7.9 Hz, 1H), 7.19 (s, 1H), 7.13 (t, J=8.0 Hz, 1H), 4.53–4.47 (m, 2H), 4.24 (m, 1H), 3.73–3.69 (m, 4H) 2.73–2.56 (m, 6H)

EXAMPLE 23
Preparation of (3-bromophenyl)-[7-(morpholine-4-ylmethyl)-[1,4]dioxano[2,3-g]quinazolin-4-yl]-amine

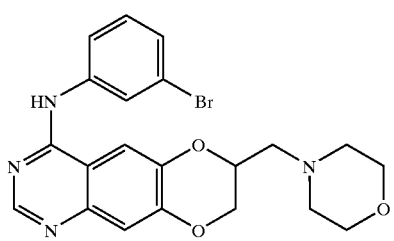

The titled compound (42 mg, 68%, m.p. 229–230° C.) was prepared in a similar manner as in Example 22, except for employing the titled compound of Example 21 (64 mg, 0.13 mmol) and morpholine.

IR(KBr) 3358, 2826, 2362, 1506, 1426, 1270, 1228 cm$^{-1}$ $^1$H NMR(300 MHz, CD$_3$OD): δ 8.41 (s, 1H), 8.11 (s, 1H), 7.83 (s, 1H), 7.70 (m, 1H), 7.28–7.26 (m, 2H), 7.17 (s, 1H), 4.87–4.45 (m, 2H), 4.19–4.45 (m, 1H), 3.72–3.66 (m, 4H), 2.7–2.54 (m, 6H)

EXAMPLE 24
Preparation of N-[4-(3-iodophenylamine)-[1,4]dioxano[2,3-g]quinazolin-7-ylmethyl]-N-(2-hydroxyethyl)]-2-ethanolamine

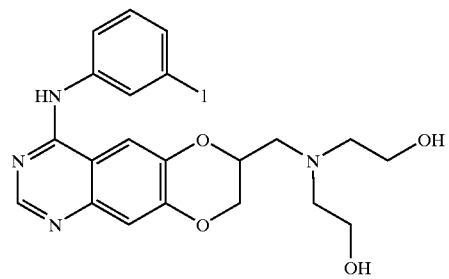

The titled compound (60 mg, 66%, m.p. 174–175° C.) was prepared in a similar manner as in Example 22, except for employing the titled compound of Example 20 (90 mg, 0.175 mmol) and bis(2-ethanol)amine.

IR(KBr): 2822, 2234, 1568, 1508, 1426, 1274, 1232 cm$^{-1}$ $^1$H NMR(300 MHz, CD$_3$OD): δ 8.40 (s, 1H), 8.24 (s, 1H), 7.85 (s, 1H), 7.76 (d, J=8.2 Hz, 1H), 7.48 (d, J=8.5 Hz, 1H), 7.19 (s, 1H), 7.13 (t, J=8.0 Hz, 1H), 4.87–4.45 (m, 2H), 4.22 (m, 1H), 3.71–3.49 (m, 4H), 3.00–2.77 (m, 6H)

EXAMPLE 25
Preparation of N-[4-(3-bromophenylamine)-[1,4]dioxano[2,3-g]quinazolin-7-ylmethyl]-N-(2-hydroxyethyl)]-2-ethanolamine

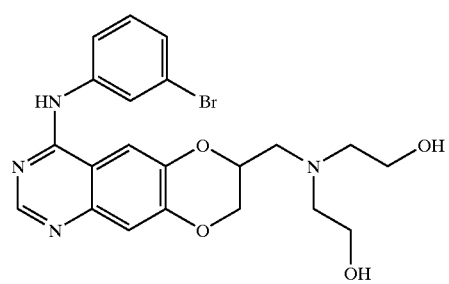

The titled compound (60 mg, 40%, m.p. 188–191° C.) was prepared in a similar manner as in Example 22, except for employing the titled compound of Example 21 (60 mg, 0.18 mmol) and bis(2-ethanol)amine.

IR(KBr): 2978, 1506, 1428, 1274, 1234 cm$^{-1}$ $^1$H NMR(300 MHz, CD$_3$OD): δ 8.41 (s, 1H), 8.10 (s, 1H), 7.84 (s, 1H), 7.76 (d, J=8.2 Hz, 1H), 7.28–7.26 (m, 2H), 7.18 (s, 1H), 4.54–4.43 (m, 2H), 4.20 (m, 1H), 3.67–3.59 (m, 4H), 2.92 (d, J=6.0 Hz, 2H), 2.89–2.73 (m, 4H)

EXAMPLE 26
Preparation of 2-[4-(3-iodophenylamine)-[1,4]dioxano[2,3-g]quinazolin-7-ylmethyl]amino-ethanol

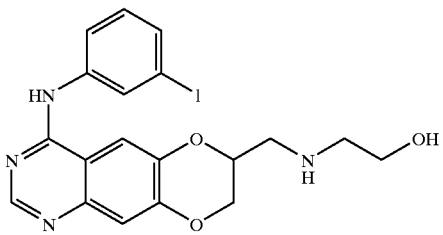

The titled compound (70 mg, 77%, m.p. 200–201° C.) was prepared in a similar manner as in Example 22, except for employing the titled compound of Example 20 (100 mg, 0.19 mmol) and 2-ethanolamine.

IR(KBr): 3094, 2910, 2838, 1568, 1508, 1424, 1268, 1240 cm$^{-1}$ $^1$H NMR(300 MHz, CD$_3$OD): δ 8.48 (s, 1H), 8.37 (s, 1H), 8.12 (s, 1H), 7.98 (d, J=8.2 Hz, 1H), 7.44 (d, J=8.1 Hz, 1H), 7.21 (s, 1H), 7.17 (t, J=8.0 Hz, 1H), 4.54–4.39 (m, 2H), 4.22–4.18 (m, 1H), 3.39 (m, 2H), 2.89–2.80 (m, 4H)

EXAMPLE 27
Preparation of 2-[4-(3-bromophenylamine)-[1,4]dioxano[2,3-g]quinazolin-7-ylmethyl]amino-ethanol

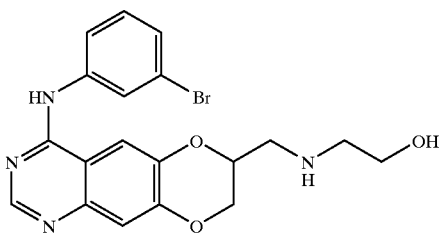

The titled compound (15 mg, 42%) was prepared in a similar manner as in Example 22, except for employing the titled compound of Example 21 (40 mg, 0.08 mmol) and 2-ethanolamine.

$^1$H NMR(300 MHz, CD$_3$OD): δ 8.42 (s, 1H), 8.10 (s, 1H), 7.88 (s, 1H), 7.71 (m, 1H), 7.28–7.27 (m, 2H), 7.20 (s, 1H), 4.51–4.43 (m, 2H), 4.17 (m, 1H), 3.69 (m, 2H), 2.97 (m, 2H), 2.82 (m, 2H)

EXAMPLE 28
Preparation of (3-bromophenyl)-[7-(4-methylpiperazin-1-yl)methyl-[1,4]dioxano[2,3-g] quinazolin-4-yl]amine

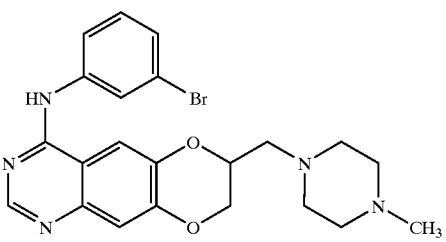

The titled compound (50 mg, 80%, m.p. 182–189° C.) was prepared in a similar manner as in Example 22, except for employing the titled compound of Example 20 (58 mg, 0.12 mmol) and N-methylpiperazine.

IR(KBr): 3270, 2940, 2796, 1510, 1424, 1278 cm$^{-1}$;

$^1$H NMR(300 MHz, CD$_3$OD): δ 8.42 (s, 1H), 8.10 (s, 1H), 7.86 (s, 1H), 7.71 (m, 1H), 7.28–7.27 (m, 2H), 7.19 (s, 1H), 4.51–4.45 (m, 2H), 4.18 (m, 1H), 2.78–2.69 (m, 110H), 2.50 (s, 3H)

EXAMPLE 29
Preparation of 2-[4-(3-bromophenylamino)-[1,4]dioxano[2,3-g]quinazolin-4-ylmethyl]amino-3-methylbutan-1-ol

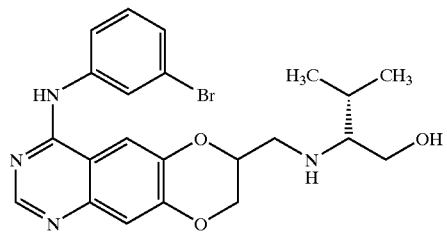

The titled compound (25 mg, 84%) was prepared in a similar manner as in Example 22, except for employing the titled compound of Example 21 (30 mg, 0.06 mmol) and (R)-valinol.

$^1$H NMR(300 MHz, CD$_3$OD): δ 8.41 (s, 1H), 8.10 (s, 1H), 7.86 (s, 1H), 7.71 (m, 1H), 7.28–7.26 (m, 2H), 7.18 (s, 1H), 4.51–4.38 (m, 2H), 4.21–4.17 (m, 1H), 3.70–3.62 (m, 2H), 3.48 (m, 1H), 3.01–2.96 (m, 2H), 1.95 (m, 1H), 0.90 (m, 6H)

EXAMPLE 30
Preparation of (3-iodophenyl)-[7-(morpholin-4-ylmethyl)-1,4]dioxano[2,3-g]quinazolin-4-yl]amine hydrochloride

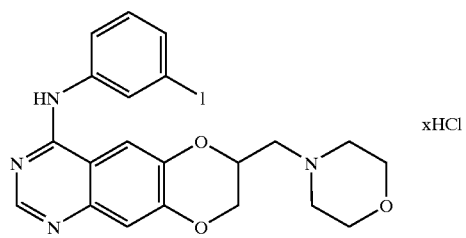

The titled compound of Example 22 (14 mg, 0.027 mmol) was dissolved in EtOH (3 ml), and then added slowly an excess amount of acetyl chloride while stirring for 2 days. Then, ether was added to the reaction mixture to obtain a solid, which was then filtered and dried under vacuum to prepare the titled compound (15 mg, 99%, m.p. 230–255° C.).

IR(KBr): 2974, 2596, 1616, 1530, 1446, 1294 cm$^{-1}$ $^1$H NMR(300 MHz, D$_2$O): 68.55 (s, 1H), 7.98 (m, 2H), 7.72 (d, J=6.8 Hz, 1H), 7.37 (s, 1H), 7.26 (t, J=8.1 Hz, 1H), 5.07 (m, 1H), 4.64 (m, 1H), 4.34 (m, 1H), 4.07 (m, 4H), 3.68–3.52 (m, 6H)

EXAMPLE 31

Preparation of (3-bromophenyl)-[7-(morpholin-4-ylmethyl)-[1,4]dioxano[2,3-g]quinazolin-4-yl]amine hydrochloride

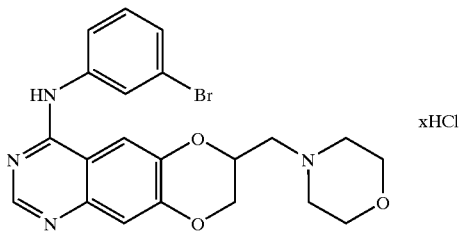

The titled compound (14 mg, 99%, m.p. 240–255° C.) was prepared in a similar manner as in Example 30, except for employing the titled compound of Example 23 (14 mg, 0.031 mmol).

IR(KBr): 3398, 2976, 2590, 1446, 1294 cm$^{-1}$ $^1$H NMR(300 MHz, D$_2$O): δ 8.52 (s, 1H), 7.97 (m, 1H), 7.77 (s, 1H), 7.54–7.39 (m, 3H), 7.35 (s, 1H), 5.04 (m, 1H), 4.61 (m, 1H), 4.34 (m, 1H), 3.96 (m, 2H), 3.77 (m, 2H), 3.59 (m, 4H)

EXAMPLE 32

Preparation of N-[4-(3-iodophenylamine)-[1,4]dioxano[2,3-g]quinazolin-7-ylmethyl]-N-(2-hydroxyethyl)]-2-ethanolamine Hydrochloride

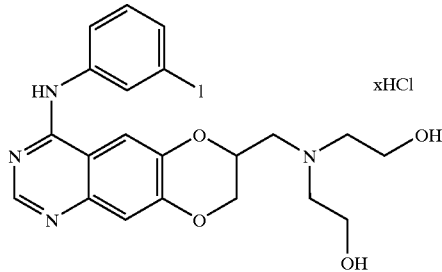

The titled compound (26 mg, 99%, m.p. 210–229° C.) was prepared in a similar manner as in Example 30, except for employing the titled compound of Example 24 (24 mg, 0.046 mmol).

IR(KBr): 3016, 2708, 1616, 1530, 1440, 1292 cm$^{-1}$ $^1$H NMR(300 MHz, D$_2$O): δ 8.72 (s, 1H), 8.30 (s, 1H), 8.16 (s, 1H), 7.73–7.67 (m, 2H), 7.33 (s, 1H), 7.23 (t, J=8.0 Hz, 1H), 5.05 (m, 1H), 4.65 (m, 1H), 4.45 (m, 1H), 3.96 (m, 4H), 3.81 (m, 2H), 3.61 (m, 4H).

EXAMPLE 33

Preparation of N-[4-(3-bromophenylamine)-[1,4]dioxano[2,3-g]quinazolin-7-ylmethyl]-N-(2-hydroxyethyl)]-2-ethanolamine hydrochloride

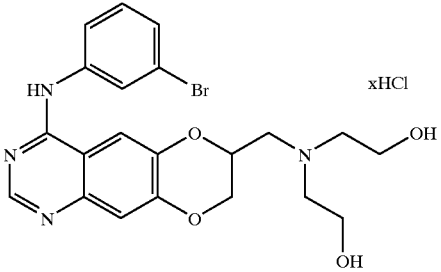

The pure titled compound (11 mg, 99%, m.p. 176–182° C. (decomposition)) was prepared in a similar manner as in Example 30, except for employing the titled compound of Example 25 (9 mg, 0.019 mmol).

IR(KBr): 3410, 3018, 2358, 1616, 1530, 1442,1290 cm$^{-1}$ $^1$H NMR(300 MHz, D$_2$O): δ 8.55 (s, 1H), 7.98 (s, 1H), 7.81 (s, 1H), 7.57–7.34 (m, 3H), 7.36 (s, 1H), 5.10 (m, 1H), 4.65 (m, 1H), 4.40 (m, 1H), 4.02 (m, 4H), 3.82 (m, 2H), 3.67 (m, 4H)

EXAMPLE 34

Preparation of 2-[4-(3-iodophenylamine)-[1,4]dioxano[2,3-g]quinazolin-7-ylmethyl]amino ethanol hydrochloride

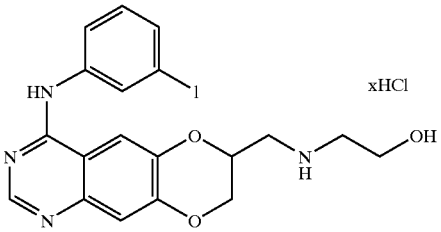

The titled compound (16 mg, 99%, m.p. 182–188° C.) was prepared in a similar manner as in Example 30, except for employing the titled compound of Example 26 (15 mg, 0.031 mmol).

IR(KBr): 3390, 3010, 2782, 1616, 1530, 1440, 1292 cm$^{-1}$ $^1$H NMR(300 MHz, D$_2$O): δ 8.54 (s, 1H), 7.96 (m, 2H), 7.73 (d, J=8.2 Hz, 1H), 7.53 (d, J=8.0 Hz, 1H), 7.37 (s, 1H), 7.25 (t, J=8.0 Hz, 1H), 4.92 (m, 1H), 4.54 (m, 2H), 4.34 (m, 1H), 3.92 (m, 2H), 3.58 (m, 2H), 3.36 (m, 2H)

EXAMPLE 35

Preparation of 2-[4-(3-bromophenylamine)-[1,4]dioxano[2,3-g]quinazolin-7-ylmethyl]amino ethanol hydrochloride

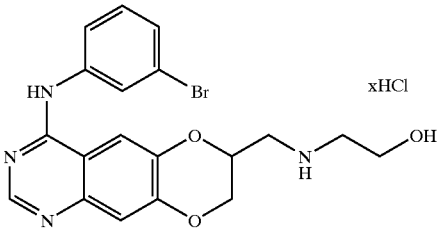

The titled compound (9 mg, 97%) was prepared in a similar manner as in Example 30, except for employing the titled compound of Example 27 (9 mg, 0.02 mmol).

IR(KBr): 3406, 3024, 2358, 1616, 1568, 1530, 1500, 1440, 1290 cm$^{-1}$ $^1$H NMR(300 MHz, D$_2$O): δ 8.09 (s, 1H), 7.53 (m, 1H), 7.34 (s, 1H) 7.12–6.96 (m, 3H), 6.90 (s, 1H), 4.45 (m, 1H), 4.18 (m, 1H), 3.90 (m, 1H), 3.46 (m, 2H), 3.10 (m, 2H), 2.90 (m, 2H)

EXAMPLE 36
Preparation of (3-iodophenyl)-[7-(4-methylpiperazin-1-yl)methyl-[1,4]dioxano[2,3-g] quinazolin-4-yl]amine hydrochloride

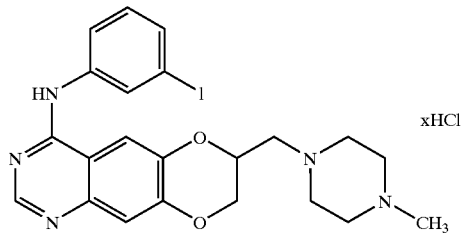

The titled compound (8 mg, 84%) was prepared in a similar manner as in Example 30, except for employing (3-iodophenyl)-[7-(4-methylpiperazin-1-yl)methyl-[1,4]dioxano[2,3-g]quinazolin-4-yl]amine (10 mg, 0.019 mmol).
$^1$H NMR(300 MHz, D$_2$O): δ 8.51 (s, 1H), 7.96 (m, 2H), 7.89 (s, 1H), 7.76 (d, J=8.3 Hz, 1H), 7.28 (d, J=7.5 Hz, 1H), 7.32 (s, 1H), 7.25 (m, 1H), 4.58–4.27 (m, 2H), 4.30–4.26 (m, 1H), 3.80–3.10 (m, 10H), 2.94 (s, 3H)

EXAMPLE 37
Preparation of (3-bromophenyl)-[7-(4-methylpiperazin-1-yl)methyl-[1,4]dioxano[2,3-g] quinazolin-4-yl]amine hydrochloride

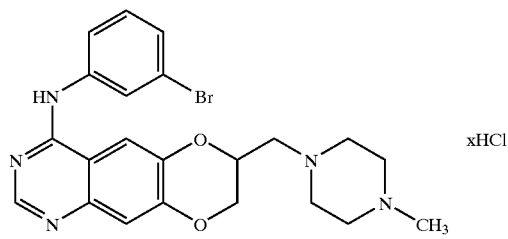

The titled compound (15 mg, 99%, m.p. 205–210° C.) was prepared in a similar manner as in Example 30, except for employing the titled compound of Example 28 (13 mg, 0.034 mmol).
IR(KBr): 3438, 2994, 2422, 1616, 1530, 1440, 1296 cm$^{-1}$
$^1$H NMR(300 MHz, D$_2$O): δ 8.42 (s, 1H), 8.10 (s, 1H), 7.86 (s, 1H), 7.71 (m, 1H), 7.28–7.27 (m, 2H), 7.19 (s, 1H), 4.86 (m, 1H), 4.64 (m, 1H), 4.33 (m, 1H), 3.70–3.30 (m, 10H), 3.02 (s, 3H, —CH3)

EXAMPLE 38
Preparation of 1-(2,3-bismethoxymethyl-benzo[1,4]dioxan-6-yl)ethanone

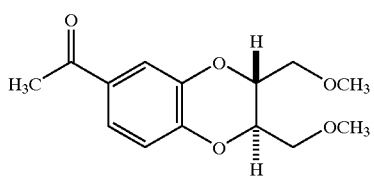

The titled compound (523 mg, 60%) was prepared in a similar manner as in Example 2, except for employing 2,3-bismethoxymethyl-benzo[1,4]dioxane (520 mg, 2.36 mmol).
$^1$H NMR(300 MHz, CDCl$_3$): δ 7.46 (d, J=2.1 Hz, 1H), 7.41 (dd, J=8.4, 2.1 Hz, 1H), 6.86 (d, J=8.4 Hz, 1H), 4.21–4.13 (m, 2H), 3.66–3.60 (m, 4H), 3.35 (s, 3H), 3.34 (s, 3H), 2.43 (s, 3H)
$^{13}$C NMR(75 MHz, CDCl$_3$): δ 197.06, 147.82, 143.01, 131.52, 122.81, 118.25, 117.52, 74.26, 73.66, 71.45 (2C), 60.08 (2C), 26.81

EXAMPLE 39
Preparation of 2,3-bismethoxymethyl-benzo[1,4]dioxane-6-carboxylic acid

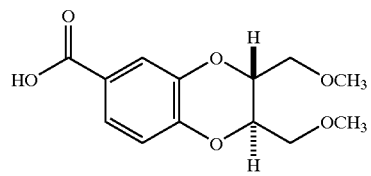

The titled compound (499 mg, 99%) was prepared in a similar manner as in Example 3, except for employing the titled compound of Example 38 (496 mg, 1.86 mmol).
$^1$H NMR(300 MHz, CDCl$_3$): δ 11.06 (br s, 1H), 7.68 (d, J=1.9 Hz, 1H), 7.62 (dd, J=8.48, 1.90 Hz, 1H), 6.96 (d, J=8.48 Hz, 1H), 4.32–4.24 (m, 2H), 3.80–3.44 (m, 4H), 3.45 (s, 3H), 3.44 (s, 3H)
$^{13}$C NMR(75 MHz, CDCl$_3$): δ 171.94, 148.40, 142.97, 124.67, 122.77, 121.87, 119.93, 117.56, 74.24, 73.54, 71.42 (2C), 60.20 (2C)

EXAMPLE 40
Preparation of 2,3-bismethoxymethyl-7-nitro-benzo[1,4]dioxane-6-carboxylic acid

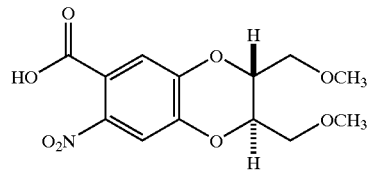

The titled compound (530 mg, 91%) was prepared in a similar manner as in Example 4, except for employing the titled compound of Example 39 (500 mg, 1.86 mmol).
$^1$H NMR(300 MHz, CDCl$_3$): δ 11.05 (br S, 1H), 7.45 (s, 1H), 7.34 (s, 1H), 4.40–4.20 (m, 2H), 3.83–3.78 (m, 4H), 3.46 (s, 3H), 3.45 (s, 3H);
$^{13}$C NMR(75 MHz, CDCl$_3$): δ 169.49, 146.50, 145.76, 143.21, 120.16, 119.46, 114.24, 74.27 (2C), 71.04 (2C), 60.07 (2C)

EXAMPLE 41
Preparation of 7-amino-2,3-bismethoxymethyl-benzo[1,4]dioxane-6-carboxylic acid

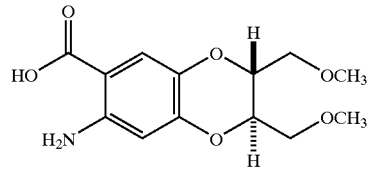

The titled compound (400 mg, 89%) was prepared in a similar manner as in Example 5, except for employing the titled compound of Example 40 (500 mg, 1.6 mmol).
$^1$H NMR(300 MHz, CDCl$_3$): δ 8.53 (br S, 2H), 7.48 (s, 1H), 6.55 (s, 1H), 4.24–4.13 (m, 2H), 3.80–3.60 (m, 4H), 3.42 (s, 3H), 3.41 (s, 3H)

EXAMPLE 42

Preparation of 7,8-bismethoxymethyl[1,4]dioxano[2,3-g]quinazolin-4-ol

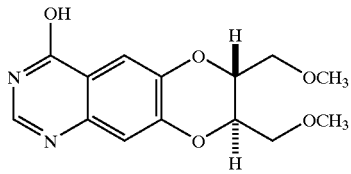

The titled compound (196 mg, 48%) was prepared in a similar manner as in Example 6, except for employing the titled compound of Example 41 (400 mg, 1.6 mmol).

$^1$H NMR(300 MHz, CDCl$_3$): δ 11.00 (br S, 1H), 7.98 (s, 1H), 7.78 (s, 1H), 7.27 (s, 1H), 4.37-4.33 (m, 2H), 3.81–3.78 (m, 4H), 3.46 (s, 6H)

EXAMPLE 43

Preparation of 4-chloro-7,8-bismethoxymethyl[1,4]dioxano[2,3-g]quinazoline

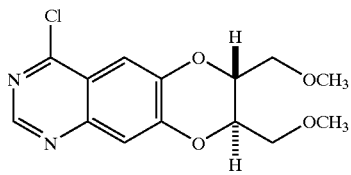

The titled compound (200 mg, 99%) was prepared in a similar manner as in Example 7, except for employing the titled compound of Example 42 (190 mg, 0.65 mmol).

EXAMPLE 44

Preparation of (7,8-bismethoxymethyl[1,4]dioxano[2,3-g]quinazolin-4-yl)-(3-bromophenyl)-amine

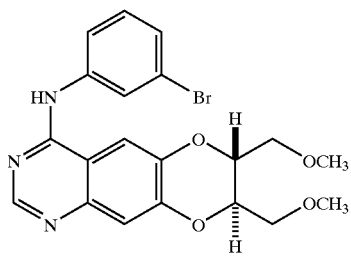

The titled compound (58 mg, 71%) was prepared in a similar manner as in Example 8, except for employing the titled compound of Example 43 (53 mg, 0.17 mmol) and 3-bromophenyl (59 mg, 0.34 mmol).

$^1$H NMR(300 MHz, DMSO-d6): δ 11.05 (s, 1H), 8.90 (s, 1H), 8.43 (s, 1H), 8.08 (s, 1H), 7.77 (d, J=5.61 Hz, 1H), 7.52–7.42 (m, 2H), 7.40 (s, 1H), 4.54–4.46 (m, 2H), 3.81–3.59 (m, 4H), 3.38 (s, 6H)

EXAMPLE 45

Preparation of (7,8-bismethoxymethyl[1,4]dioxano[2,3-g]quinazolin-4-yl)-(3-iodophenyl)amine

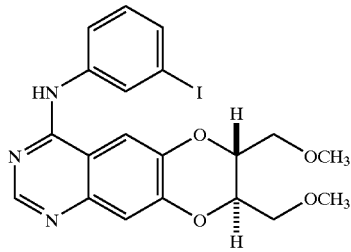

The titled compound (63 mg, 70%) was prepared in a similar manner as in Example 8, except for employing the titled compound of Example 43 (50 mg, 0.17 mmol) and 3-iodophenyl (75 mg, 0.34 mmol).

$^1$H NMR(300 MHz, DMSO-d6): δ 11.05 (s, 1H), 8.88 (s, 1H), 8.42 (s, 1H), 8.19 (s, 1H), 7.79 (d, J=7.9 Hz, 1H), 7.66 (d, J=7.9 Hz, 1H), 7.41 (s, 1H), 7.28 (m, 1H), 4.53–4.44 (m, 2H), 3.79–3.70 (m, 4H), 3.38 (s, 6H)

EXAMPLE 46

Preparation of (7,8-bismethoxymethyl[1,4]dioxano[2,3-g]quinazolin-4-yl)-(3-chlorophenyl)-amine

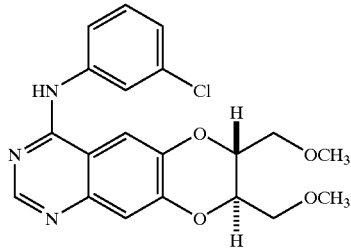

The titled compound (52 mg, 71%) was prepared in a similar manner as in Example 8, except for employing the titled compound of Example 43 (49 mg, 0.168 mmol) and 3-chlorophenyl (43 mg, 0.34 mmol).

$^1$H NMR(300 MHz, DMSO-d6): δ 11.14 (s, 1H), 8.90 (s, 1H), 8.45 (s, 1H), 7.94 (s, 1H), 7.72 (d, J=7.37 Hz, 1H), 7.51 (m, 1H), 7.42 (s, 1H), 7.38 (d, J=7.9 Hz, 1H), 4.54–4.47 (m, 2H), 3.80–3.68 (m, 4H), 3.38 (s, 6H)

EXAMPLE 47

Preparation of (7,8-bismethoxymethyl[1,4]dioxano[2,3-g]quinazolin-4-yl)-[3-(trimethylsilylethynyl)phenyl]-amine

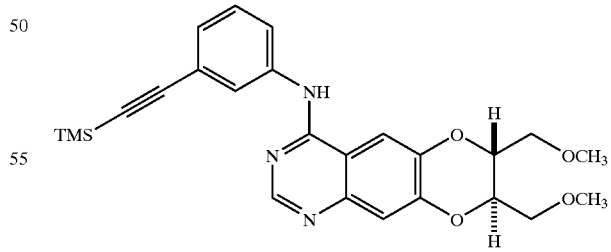

3 ml of trimethylamine was mixed with the titled compound of Example 45 (40 mg, 0.075 mmol), 1-trimethylsilylacetylene (15 mg, 0.15 mmol), copper iodide (16 mg, 0.084 mmol) and tetrakis(triphenylphosphine)palladium (26 mg, 0.022 mmol), followed by stirring for 12 hours at a room temperature. Then, the reaction mixture was filtered to obtain a filtrate, which was then concentrated and purified by a column chromatography (mobile phase:

hexane:ethylacetate=2:3(v:v)) to prepare the titled compound (33 mg, 97%).

$^1$H NMR(300 MHz, CDCl$_3$): δ 8.71 (s, 1H), 7.83 (s, 1H), 7.73 (d, J=7.7 Hz, aniline 1H), 7.57 (s, 1H), 7.39–7.09 (m, 4H), 4.33 (m, 2H), 3.76–3.70 (m, 4H), 3.44 (s, 3H), 3.43 (s, 3H)

EXAMPLE 48

Preparation of (7,8-bismethoxymethyl[1,4]dioxano[2,3-g]quinazolin-4-yl)-[3-(ethynyl)phenyl]-amine

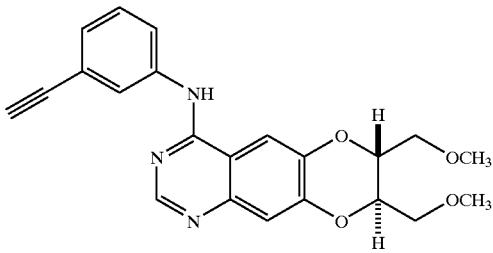

The titled compound of Example 47 (34 mg, 0.073 mmol) was dissolved in 5 ml of methanol, and then added potassium carbonate (26 mg), followed by stirring for 24 hours at a room temperature. Water was added to the reaction mixture, which was then extracted with methylene chloride, dried over MgSO$_4$ and concentrated. The resulting residue was purified by a column chromatography(mobile phase: hexane:ethylacetate:methanol=20:30:1 (v:v:v)) to prepare the titled compound (6 mg, 21%).

$^1$H NMR(300 MHz, CDCl$_3$): δ 8.65 (s, 1H), 7.90 (s, 1H), 7.75–7.28 (m, 6H), 4.38 (m, 2H), 4.01–3.75 (m, 4H), 3.46 (s, 6H)

EXAMPLE 49

Measurement of the Solubility of Compounds in Water

By employing the conventionally known material, DP153035, as a standard material, the solubilities of compounds of the general formula(I) prepared in the above Examples 8, 10, 12, 13, 16, 18, 30, 31, 33, 34, 35 and 36 were measured, respectively. That is, 1 mg of each of the above compounds was completely dissolved in 1 ml of DMSO, which was then subjected to HPLC employing C$_{18}$ resin, and the peak area of chromatogram was calculated. And then, 1 mg of each of the same compound was dissolved in 10 ml of DMSO, which was then subjected to the same HPLC as the above to obtain a chromatogram, and the peak area was calculated therefrom. A solubility calibration curve was prepared by employing the above two data, and a linear function was deduced from that to complete a calibration curve (X axis: area, Y axis: logarithm value of concentration).

Each of the same compounds was supersaturated in 1 ml of water, which was then centrifuged at 14,000 rpm for 1 min. The precipitate was separated from the supernatant which was then subjected to the same HPLC as the above to obtain a chromatogram, and the peak area was calculated therefrom. The obtained value was substituted to the above calibration curve to measure the solubility by mg/10 ml of water (see: Table 1).

TABLE 1

The solubility of compounds in water

| Example | Solubility (mg/10 ml of water) |
| --- | --- |
| 8 | 10.40 |
| 10 | 2.41 |
| 12 | 0.74 |
| 13 | 0.08 |
| 16 | 4.57 |
| 18 | 0.45 |
| 30 | >>1,000 |
| 31 | >>1,000 |
| 33 | >>1,000 |
| 34 | >>1,000 |
| 35 | >>1,000 |
| 36 | >>1,000 |
| DP153035 | 0.20 |

As shown in Table 1 above, it was clearly demonstrated that most compounds of the present invention have a better water solubility than the standard material, DP153035.

EXAMPLE 51

Inhibition of EGFR Tyrosine Kinase

By employing the conventionally known material, DP153035, as a standard material, compounds of the general formula(I) prepared in the above Examples 8, 10, 12, 13, 15, 17, 18, 22, 23, 25, 27, 28, 29, 31, 33, 35, 37, 44, 45, 46 and 48 were tested for the inhibitory effect on EGFR tyrosine kinase. The test was accomplished in a 20 μl reaction volume using 0.1 unit per reaction of purified human EGFR kinase (Promega, U.S.A.) and 50 μM biotin-conjugated substrate for tyrosine kinase (Promega, U.S.A.) and, 50 μM P$^{32}$-γ-ATP (0.2 μCi) and 20 mM Tris-HCl (pH 7.5) were employed as an ATP and a reaction solution, respectively. The test was carried out at 30° C. for 10 min, and terminated by the addition of 10 μl of 30% phosphate solution. The half of the reaction product was spotted onto avidin-layered PVDF membrane, which was then washed with 20 mM Tris-HCl (pH 8.0) and 0.2N NaCl aqueous solution for more than 2 hours. After that, the reaction product was quantitated with BAS (Kodak, Japan) and the concentration of the compound by which EGFR tyrosine kinase activity is 50% inhibited was represented as IC$_{50}$. see: Table 2.

TABLE 2

Inhibitory effect on EGFR tyrosine kinase

| Example | EGFR IC$_{50}$ (ng/ml) |
| --- | --- |
| 8 | >100 |
| 10 | 14.28 |
| 12 | >100 |
| 13 | 13.6 |
| 15 | >100 |
| 17 | 36.71 |
| 18 | 1.58 |
| 22 | 12.67 |
| 23 | 28.86 |
| 25 | 47.53 |
| 27 | 12.16 |
| 28 | 4.19 |
| 29 | >100 |
| 31 | 46.18 |
| 33 | 21.33 |
| 35 | 21.53 |
| 37 | 57.98 |
| 44 | 33.07 |
| 45 | >100 |
| 46 | >100 |

TABLE 2-continued

Inhibitory effect on EGFR tyrosine kinase

| Example | EGFR $IC_{50}$ (ng/ml) |
|---|---|
| 48 | >100 |
| DP153035 | 2.74 |

As shown in Table 2, it was clearly demonstrated that most compounds of the present invention have a lower inhibitory effect on EGFR tyrosine kinase than the standard material, while the compound of Example 18 has a higher inhibitory effect than the standard material and the compound of Example 28 has a similar inhibitory activity to that the standard material.

EXAMPLE 52

Inhibition of Cancer Cell Growth

A431 cancer cell was cultivated at 37° C. under an environment of 5% (v/v) $CO_2$ employing RPMI 1640 medium containing 10% (v/v) fetal calf serum. Approximately 1000 of cultured cells was transferred to 96 well plate, grown overnight and treated with a standard material, DP153035, and the compounds prepared in Examples 8, 10, 12, 13, 15, 17, 18, 22, 23, 25, 27, 28, 29, 31, 33, 35, 37, 44, 45, 46 and 48. The above cells was grown again for 2 days, and then, fixed with formalin solution (Sigma Chem. Co., U.S.A.) and washed with water. After that, the cells was dried in the atmosphere, stained with 0.1% (v/v) sulforhodamine B solution (Sigma Chem. Co., U.S.A.) for 30 min and wash with 1% (v/v) acetic acid aqueous solution. Then, dye attached to cells was extracted with 0.1M Tris-HCl (pH 8.0) and the absorbances of the remaining culture were measured at 520 nm by the aid of microplate reader. And then, the concentration of the compound by which cell growth is 50% inhibited was represented as $GI_{50}$(s: Table 3).

TABLE 3

Inhibitory effect of A431 cancer cell growth

| Example | A431 $GI_{50}$ (μg/ml) |
|---|---|
| 8 | 1.16 |
| 10 | 0.24 |
| 12 | 0.43 |
| 13 | 0.21 |
| 15 | 0.06 |
| 17 | 0.60 |
| 18 | 1.98 |
| 22 | 0.38 |
| 23 | 0.13 |
| 25 | 0.61 |
| 27 | 0.22 |
| 28 | 0.22 |
| 29 | 1.90 |
| 31 | 0.19 |
| 33 | 0.67 |
| 35 | 0.95 |
| 37 | 0.38 |
| 44 | 2.91 |
| 45 | 1.59 |
| 46 | 2.37 |
| 48 | 1.89 |
| DP153035 | 0.99 |

As shown in Table 3, it was clearly demonstrated that the compounds prepared in the above Examples 10, 12, 13, 15, 17, 22, 23, 25, 27, 28, 31, 33, 35 and 37 have a better inhibitory effect of cancer cell growth than the standard material.

As clearly illustrated and demonstrated above, the present invention provides 4-(phenylamino)-[1,4]dioxano[2,3-g] quinazoline derivatives which inhibit the activity of tyrosine kinase of epidermal growth factor receptor(EGFR), and pharmaceutically acceptable salts, hydrates and solvates thereof, and a process for preparing the same. Since 4-(phenylamino)-[1,4]dioxano[2,3-g]quinazoline derivatives of the invention have a high solubility in water and inhibit the activity of EGFR tyrosine kinase and the growth of cancer cells, they can be practically applied in the treatment of overproliferation-associated diseases such as cancer.

What is claimed is:

1. A compound that has Formula I:

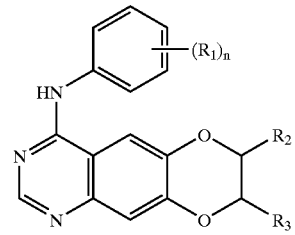

Formula (I)

or a pharmaceutically acceptable salt, hydrate or solvate thereof, wherein:

n is 1, 2 or 3;

$R_1$ is substituent group, may be identical or different when n is 2 or 3, and is selected from the group consisting of hydrogen, halogen, $C_{1-6}$-alkyl, $C_{3-6}$-cycloalkyl, hydroxy, $C_{1-6}$-alkoxy, $C_{3-6}$-cycloalkoxy, (aryl or heteroaryl)oxy, $C_{1-6}$-thioalkoxy, $C_{3-6}$-thiocycloalkoxy, thio(aryl or heteroaryl)oxy, nitro, amino, N-mono($C_{1-6}$)-alkylamino, N,N-di($C_{1-6}$)-alkylamino, formamido, amido, acetamido, hydroxyamino, $C_{1-6}$-alkoxyamino, hydrazino, trifluoromethyl, trifluoromethoxy, alkenyl, alkynyl, aryl and heterocyclic; and $R_2$ and $R_3$ are substituent groups of —$(CH_2)_m$—$R_4$ and may be identical or different, wherein:

m is 0 or 1, and $R_4$ is selected from the group consisting of hydrogen, halogen, $C_{1-6}$-alkyl, $C_{3-6}$-cycloalkyl, hydroxy, $C_{1-6}$-alkoxy, $C_{3-6}$-cycloalkoxy, $C_{1-6}$-thioalkoxy, $C_{3-6}$-thiocycloalkoxy, amino, mono-($C_{1-6}$)-alkylamino, di-($C_{1-6}$)-alkylamino, formamido, nitro, hydroxyamino, $C_{1-6}$-alkoxyamino, hydrazino, cyano, carboxyl, alkoxycarbonyl, amido, N-mono-($C_{1-6}$)-alkylamido, N,N-di-($C_{1-6}$)-alkylamido, thioamido, N-mono-($C_{1-6}$)-alkylthioamido, N,N-di-($C_{1-6}$)-alkylthioamido, guanidino, ureido, $C_{1-6}$-alkylsulfido, $C_{1-6}$-alkylsulfonyl, trifluoromethyl, trifluoromethoxy, morpholino, 4-$C_{1-6}$-alkylpiperidino, mono[hydroxy($C_{1-6}$)-alkyl]amino, di[hydroxy-($C_{1-6}$)-alkyl]amino, mono[pyrrolidine-($C_{1-6}$)-alkyl]amino, and di[pyrrolidine-($C_{1-6}$)-alkyl] amino or —$N(R_5)(CHR_6R_7)$, wherein $R_5$ is hydrogen or $C_{1-6}$-alkyl, $R_6$ is $(CH_2)_n$OH where n is an integer of 1 to 4, and $R_7$ is selected from the group consisting of hydrogen, $C_{1-5}$-alkyl, hydroxy-($C_{1-5}$)-alkyl, thiohydroxy-($C_{1-5}$)-alkyl, phenyl-($C_{1-5}$)-alkyl, 4-hydroxyphenyl-($C_{1-5}$)-alkyl and heteroaryl-($C_{1-5}$)-alkyl, wherein at least one of $R_2$ and $R_3$ is other than hydrogen.

2. The compound of claim 1, or a pharmaceutically acceptable salt, hydrate or solvate thereof, wherein the pharmaceutically acceptable salt comprises an inorganic acid salt, an organic acid salt or a sulfonic acid salt of the compound.

3. The compound of claim 2, or a pharmaceutically acceptable salt, hydrate or solvate thereof, wherein the inorganic acid salt is one or more selected from the group consisting of a hydrochloric acid salt, a hydrobromic acid salt, a hydroiodic acid salt, a sulfuric acid salt, a nitric acid salt and a phosphoric acid salt.

4. The compound of claim 2, or a pharmaceutically acceptable salt, hydrate or solvate thereof, wherein the organic acid salt is one or more selected from the group consisting of an acetic acid salt, a succinic acid salt, a tartaric acid salt, a malic acid salt, a formic acid salt, a citric acid salt, a trichloroacetic acid salt, a trifluoroacetic acid salt, a gluconic acid salt, a lactic acid salt, a fumaric acid salt, a picric acid salt and a maleic acid salt.

5. The compound of claim 2, or a pharmaceutically acceptable salt, hydrate or solvate thereof, wherein the sulfonic acid salt is one or more selected from the group consisting of a methane sulfonic acid salt, a benzene sulfonic acid salt, a p-toluene sulfonic acid salt and a naphthalene sulfonic acid salt.

6. A compound or a pharmaceutically acceptable salt, hydrate or solvate thereof, wherein the compound is selected from the group consisting of:
 (3-bromophenyl)-(7-methoxymethyl-[1,4]-dioxano[2,3-g]quinazolin-4-yl)-amine,
 (3,5-dichlorophenyl)-(7-methoxymethyl-[1,4]-dioxano[2,3-g]quinazolin-4-yl)-amine,
 (3,5-dimethylphenyl)-(7-methoxymethyl-[1,4]-dioxano[2,3-g]quinazolin-4-yl)-amine,
 (3,4,5-trifluorophenyl)-(7-methoxymethyl-[1,4]-dioxano[2,3-g]quinazolin-4-yl)-amine,
 (3-iodophenyl)-[7-(morpholin-4-yl-methyl)-[1,4]dioxano[2,3-g]quinazolin-4-yl]-amine,
 (3-bromophenyl)-[7-(morpholin-4-yl-methyl)-[1,4]dioxano[2,3-g]quinazolin-4-yl]-amine,
 (3-bromophenyl)-[7-(morpholin-4-yl-methyl)-[1,4]dioxano[2,3-g]quinazolin-4-yl]-amine hydrochloride,
 2-[4-(3-bromophenylamine)-[1,4]dioxano[2,3-g]quinazolin-7-yl-methyl]-aminoethanol, and
 (3-bromophenyl)-[7-(4-methylpiperazin-1-yl) methyl-[1,4]dioxano[2,3-g]quinazolin-4-yl]-amine.

7. A process for preparing the compound of claim 1, or a pharmaceutically acceptable salt, hydrate or solvate thereof, the process comprising: providing a quinazoline derivative of Formula (II) and a substituted aniline of Formula (III):

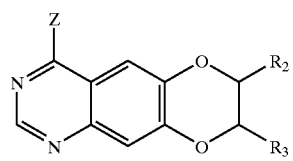

Formula (II)

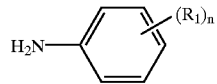

Formula (III)

wherein Z is halogen, alkoxy, aryloxy or sulfonyloxy;
 mixing the quinazoline derivative and the substituted aniline in the presence of an organic solvent to provide a liquid mixture; and
 adding an acid to the liquid mixture, thereby forming the compound, or a pharmaceutically acceptable salt, hydrate or solvate thereof.

8. The process of claim 7, wherein in the mixing 1 equi. of the quinazoline derivative and 2 equi. of the substituted aniline are mixed together.

9. The process of claim 7, wherein the organic solvent is an inert organic solvent.

10. The process of claim 7, wherein the organic solvent is selected from the group consisting of an alkanol, an ester, a halogenated solvent, an ether, an aromatic solvent, N,N-dimethylformamide, and mixtures of the foregoing.

11. The process of claim 7, wherein the acid is hydrochloric acid.

12. The process of claim 7, further comprising maintaining the mixture after the addition of the acid at a temperature from about 20° C. to about 80° C.

13. A pharmaceutical composition comprising a pharmaceutical carrier and the compound of claim 1, or a pharmaceutically acceptable salt, hydrate or solvate thereof.

14. A method of causing inhibitory effect on tyrosine kinase, comprising administering to a patient in need of such inhibition a composition comprising a pharmaceutically acceptable carrier and a pharmaceutically effective amount of the compound of claim 1, or a pharmaceutically acceptable salt, hydrate or solvate thereof.

15. A method of causing inhibitory effect on tyrosine kinase, comprising administering to a patient in need of such inhibition a composition comprising a pharmaceutically acceptable carrier and a pharmaceutically effective amount of a compound, or a pharmaceutically acceptable salt, hydrate or solvate thereof, wherein the compound, or a pharmaceutically acceptable salt, hydrate or solvate thereof, is selected from the group consisting of:
 (3-bromophenyl)-(7-methoxymethyl-[1,4]-dioxano[2,3-g]quinazolin-4-yl)-amine,
 (3,5-dichlorophenyl)-(7-methoxymethyl-[1,4]-dioxano[2,3-g]quinazolin-4-yl)-amine,
 (3,5-dimethylphenyl)-(7-methoxymethyl-[1,4]-dioxano[2,3-g]quinazolin-4-yl)-amine,
 (3,4,5-trifluorophenyl)-(7-methoxymethyl-[1,4]-dioxano[2,3-g]quinazolin-4-yl)-amine,
 (3-iodophenyl)-[7-(morpholin-4-yl-methyl)-[1,4]dioxano[2,3-g]quinazolin-4-yl]-amine,
 (3-bromophenyl)-[7-(morpholin-4-yl-methyl)-[1,4]dioxano[2,3-g]quinazolin-4-yl]-amine,
 (3-bromophenyl)-[7-(morpholin-4-yl-methyl)-[1,4]dioxano[2,3-g]quinazolin-4-yl]-amine hydrochloride,
 2-[4-(3-bromophenylamine)-[1,4]dioxano[2,3-g]quinazolin-7-yl-methyl]-aminoethanol, and
 (3-bromophenyl)-[7-(4-methylpiperazin-1-yl) methyl-[1,4]dioxano[2,3-g]quinazolin-4-yl]-amine.

16. The method of claim 14, wherein the pharmaceutically acceptable salt comprises an inorganic acid salt, organic acid salt or sulfonic acid salt of the compound.

17. A method of inhibiting cancer cell growth, wherein said growth is effected by tyrosine kinase, the method comprising administering to a patient in need of such inhibition a composition comprising a pharmaceutically acceptable carrier and a pharmaceutically effective amount of the compound of claim 1, or a pharmaceutically acceptable salt, hydrate or solvate thereof.

18. A method of inhibiting cancer cell growth, wherein said growth is effected by tyrosine kinase, the method comprising administering to a patient in need of such inhibition a composition comprising a pharmaceutically acceptable carrier and a pharmaceutically effective amount of a compound, or a pharmaceutically acceptable salt, hydrate or solvate thereof, wherein the compound, or a pharmaceutically acceptable salt, hydrate or solvate thereof, is selected from the group consisting of:

(3-bromophenyl)-(7-methoxymethyl-[1,4]-dioxano[2,3-g]quinazolin-4-yl)-amine, (3,5-dichlorophenyl)-(7-methoxymethyl-[1,4]-dioxano[2,3-g]quinazolin-4-yl)-amine, (3,5-dimethylphenyl)-(7-methoxymethyl-[1,4]-dioxano[2,3-g]quinazolin-4-yl)-amine, (3,4,5-trifluorophenyl)-(7-methoxymethyl-[1,4]-dioxano[2,3-g]quinazolin-4-yl)-amine, (3-iodophenyl)-[7-(morpholin-4-yl-methyl)-[1,4]dioxano[2,3-g]quinazolin-4-yl]-amine, (3-bromophenyl)-[7-(morpholin-4-yl-methyl)-[1,4]dioxano[2,3-g]quinazolin-4-yl]-amine, (3-bromophenyl)-[7-(morpholin-4-yl-methyl)-[1,4]dioxano[2,3-g]quinazolin-4-yl]-amine hydrochloride, 2-[4-(3-bromophenylamine)-[1,4]dioxano[2,3-g]quinazolin-7-yl-methyl]-aminoethanol, and (3-bromophenyl)-[7-(4-methylpiperazin-1-yl) methyl-[1,4]dioxano[2,3-g]quinazolin-4-yl]-amine.

19. The method of claim 17, wherein the pharmaceutically acceptable salt comprises an inorganic acid salt, organic acid salt or sulfonic acid salt of the compound.

* * * * *